US011980554B2

(12) United States Patent
Tieu et al.

(10) Patent No.: US 11,980,554 B2
(45) Date of Patent: May 14, 2024

(54) STENT

(71) Applicant: Terumo Corporation, Tokyo (JP)

(72) Inventors: Tai D. Tieu, Tokyo (JP); Gregory M. Cruise, Tokyo (JP); Heather Griffith, Tokyo (JP); Helen Nguyen, Tokyo (JP); Minh Nguyen, Tokyo (JP); Ponaka Pung, Tokyo (JP); Shirley Vong, Tokyo (JP)

(73) Assignee: Terumo Corporation, Tokyo (JP)

( * ) Notice: Subject to any disclaimer, the term of this patent is extended or adjusted under 35 U.S.C. 154(b) by 214 days.

(21) Appl. No.: 17/379,695

(22) Filed: Jul. 19, 2021

(65) Prior Publication Data

US 2021/0346181 A1    Nov. 11, 2021

Related U.S. Application Data

(63) Continuation of application No. 17/244,499, filed on Apr. 29, 2021, now Pat. No. 11,291,566, which is a
(Continued)

(51) Int. Cl.
*A61F 2/90* (2013.01)
*A61F 2/852* (2013.01)
(Continued)

(52) U.S. Cl.
CPC ............. *A61F 2/86* (2013.01); *A61F 2/852* (2013.01); *A61F 2/88* (2013.01); *A61F 2/90* (2013.01); *A61F 2/966* (2013.01); *D04C 1/06* (2013.01); *D04C 3/48* (2013.01); *A61F 2002/823* (2013.01); *A61F 2002/826* (2013.01); *A61F 2002/828* (2013.01); *A61F 2/91* (2013.01); *A61F 2/945* (2013.01);
(Continued)

(58) Field of Classification Search
CPC .... A61F 2/852; A61F 2/86; A61F 2/90; A61F 2002/828
See application file for complete search history.

(56) References Cited

U.S. PATENT DOCUMENTS

| 4,130,904 A | 12/1978 | Whalen |
| 4,655,771 A | 4/1987 | Wallsten |

(Continued)

FOREIGN PATENT DOCUMENTS

| EP | 1214917 A1 | 6/2002 |
| EP | 1374799 A1 | 1/2004 |

(Continued)

OTHER PUBLICATIONS

United States Patent and Trademark Office, Office Action dated Jul. 22, 2021 in U.S. Appl. No. 16/590,252, 18 pages.
(Continued)

*Primary Examiner* — Suba Ganesan
(74) *Attorney, Agent, or Firm* — Inskeep IP Group, Inc.

(57) ABSTRACT

In one embodiment according to the present invention, a stent is described having a generally cylindrical body formed from a single woven nitinol wire. The distal and proximal ends of the stent include a plurality of loops, some of which include marker members used for visualizing the position of the stent. In another embodiment, the previously described stent includes an inner flow diverting layer.

20 Claims, 16 Drawing Sheets

Related U.S. Application Data continuation of application No. 16/590,252, filed on Oct. 1, 2019, now Pat. No. 11,351,046, which is a continuation of application No. 15/784,052, filed on Oct. 13, 2017, now Pat. No. 10,463,515, which is a continuation of application No. 13/311,430, filed on Dec. 5, 2011, now Pat. No. 9,867,725, which is a continuation-in-part of application No. 13/003,277, filed as application No. PCT/US2010/061627 on Dec. 21, 2010, now abandoned.

(60) Provisional application No. 61/422,604, filed on Dec. 13, 2010, provisional application No. 61/425,175, filed on Dec. 20, 2010, provisional application No. 61/427,773, filed on Dec. 28, 2010.

(51) Int. Cl.
| | | |
|---|---|---|
| *A61F 2/86* | (2013.01) | |
| *A61F 2/88* | (2006.01) | |
| *A61F 2/966* | (2013.01) | |
| *D04C 1/06* | (2006.01) | |
| *D04C 3/48* | (2006.01) | |
| *A61F 2/82* | (2013.01) | |
| *A61F 2/91* | (2013.01) | |
| *A61F 2/945* | (2013.01) | |

(52) U.S. Cl.
CPC ............... *A61F 2210/0076* (2013.01); *A61F 2230/0021* (2013.01); *A61F 2230/005* (2013.01); *A61F 2230/0054* (2013.01); *A61F 2230/0058* (2013.01); *A61F 2230/0067* (2013.01); *A61F 2240/001* (2013.01); *A61F 2250/0023* (2013.01); *A61F 2250/0036* (2013.01); *A61F 2250/0039* (2013.01); *A61F 2250/0098* (2013.01); *D10B 2509/06* (2013.01)

(56) References Cited

U.S. PATENT DOCUMENTS

| | | |
|---|---|---|
| 4,768,507 A | 9/1988 | Fischell et al. |
| 4,856,516 A | 8/1989 | Hillstead |
| 4,994,069 A | 2/1991 | Ritchart et al. |
| 5,026,377 A | 6/1991 | Burton et al. |
| 5,064,435 A | 11/1991 | Porter |
| 5,133,731 A | 7/1992 | Butler et al. |
| 5,158,548 A | 10/1992 | Lau et al. |
| 5,226,911 A | 7/1993 | Chee et al. |
| 5,312,415 A | 5/1994 | Palermo |
| 5,382,259 A | 1/1995 | Phelps et al. |
| 5,382,260 A | 1/1995 | Dormandy, Jr. et al. |
| 5,383,925 A | 1/1995 | Schmitt |
| 5,476,472 A | 12/1995 | Dormandy, Jr. et al. |
| 5,578,074 A | 11/1996 | Mirigian |
| 5,582,619 A | 12/1996 | Ken |
| 5,609,627 A | 3/1997 | Goicoechea et al. |
| 5,624,461 A | 4/1997 | Mariant |
| 5,645,558 A | 7/1997 | Horton |
| 5,658,308 A | 8/1997 | Snyder |
| 5,702,418 A | 12/1997 | Ravenscroft |
| 5,718,711 A | 2/1998 | Berenstein et al. |
| 5,951,599 A | 9/1999 | McCrory |
| 6,143,022 A | 11/2000 | Shull et al. |
| 6,287,333 B1 | 9/2001 | Appling et al. |
| 6,342,068 B1 | 1/2002 | Thompson |
| 6,428,569 B1 | 8/2002 | Brown |
| 6,582,460 B1 | 6/2003 | Cryer |
| 6,626,939 B1 | 9/2003 | Burside et al. |
| 6,645,239 B1* | 11/2003 | Park .................. A61F 2/95 623/1.22 |
| 6,746,468 B1 | 6/2004 | Sepetka et al. |
| 6,818,013 B2 | 11/2004 | Mitelberg et al. |
| 7,037,331 B2 | 5/2006 | Mitelberg et al. |
| 7,195,648 B2 | 3/2007 | Jones et al. |
| 7,311,726 B2 | 12/2007 | Mitelberg et al. |
| 7,517,361 B1 | 4/2009 | Ravenscroft |
| 7,942,925 B2 | 5/2011 | Yodfat et al. |
| 8,382,825 B2 | 2/2013 | Garcia et al. |
| 8,419,787 B2 | 4/2013 | Yodfat et al. |
| 2001/0000188 A1 | 4/2001 | Lenker et al. |
| 2001/0025195 A1 | 9/2001 | Shaolian et al. |
| 2002/0169473 A1 | 11/2002 | Sepetka et al. |
| 2003/0149473 A1 | 8/2003 | Chouinard et al. |
| 2003/0216807 A1 | 11/2003 | Jones et al. |
| 2004/0098095 A1 | 5/2004 | Burnside et al. |
| 2004/0215332 A1 | 10/2004 | Frid |
| 2004/0243221 A1 | 12/2004 | Fawzi et al. |
| 2005/0137680 A1 | 6/2005 | Ortiz et al. |
| 2005/0240261 A1 | 10/2005 | Rakos et al. |
| 2005/0256563 A1* | 11/2005 | Clerc .................. B23K 9/0026 623/1.16 |
| 2006/0116750 A1 | 6/2006 | Hebert et al. |
| 2006/0122685 A1 | 6/2006 | Bonsignore et al. |
| 2006/0206201 A1 | 9/2006 | Garcia et al. |
| 2007/0168019 A1 | 7/2007 | Amplatz et al. |
| 2007/0179590 A1 | 8/2007 | Lu et al. |
| 2007/0207186 A1 | 9/2007 | Scanlon et al. |
| 2007/0276470 A1 | 11/2007 | Tenne |
| 2008/0109063 A1 | 5/2008 | Hancock et al. |
| 2008/0221671 A1 | 9/2008 | Chouinard et al. |
| 2009/0099643 A1 | 4/2009 | Hyodoh et al. |
| 2009/0171443 A1 | 7/2009 | Kuppurathanam et al. |
| 2009/0177264 A1 | 7/2009 | Ravenscroft |
| 2009/0177268 A1 | 7/2009 | Lundkuist et al. |
| 2009/0187240 A1 | 7/2009 | Clerc et al. |
| 2009/0192588 A1 | 7/2009 | Shin et al. |
| 2009/0198315 A1 | 8/2009 | Boudjemline |
| 2009/0270974 A1 | 10/2009 | Berez et al. |
| 2009/0287300 A1 | 11/2009 | Dave et al. |
| 2009/0312834 A1 | 12/2009 | Wood et al. |
| 2009/0326640 A1 | 12/2009 | Yoshimura et al. |
| 2010/0049302 A1 | 2/2010 | Kang et al. |
| 2011/0022149 A1 | 1/2011 | Cox et al. |
| 2011/0054589 A1* | 3/2011 | Bashiri .................. A61F 2/90 623/1.15 |
| 2011/0093002 A1 | 4/2011 | Rucker et al. |
| 2011/0152998 A1 | 6/2011 | Berez et al. |
| 2017/0112643 A1 | 4/2017 | Cattaneo et al. |

FOREIGN PATENT DOCUMENTS

| | | |
|---|---|---|
| JP | 10286312 | 10/1998 |
| JP | 2008173461 A | 7/2008 |
| WO | WO 94/06373 A1 | 3/1994 |
| WO | WO1999/002092 A2 | 1/1999 |
| WO | WO2000/044308 A2 | 8/2000 |
| WO | WO2006/130352 A2 | 8/2000 |
| WO | WO 03/011184 A2 | 2/2003 |
| WO | WO 03/105728 A1 | 12/2003 |
| WO | WO 2004/071736 A2 | 8/2004 |
| WO | WO2004/071736 A2 | 8/2004 |
| WO | WO 2006/130352 A2 | 12/2006 |
| WO | WO2008/111716 A1 | 9/2008 |
| WO | WO 2008/118132 A1 | 10/2008 |
| WO | WO2009/089218 A2 | 7/2009 |
| WO | WO 2010/120926 A1 | 10/2010 |
| WO | WO 2012/025247 A1 | 3/2012 |

OTHER PUBLICATIONS

United States Patent and Trademark Office, Office Action dated Aug. 3, 2021 in U.S. Appl. No. 17/244,499, 16 pages.

Brazil Patent Office, Preliminary Office Action dated Dec. 8, 2020 with English translation in Brazilian Patent Application No. BR112013014836-5, 8 pages.

European Patent Office, "Decision to maintain the European patent in amended form (Art. 101(3)(a) EPC", *in re Opposition by Pronovem Luxembourg s.a. to European Application No. 13761575.3*, Jan. 23, 2020, 2 pages.

(56) References Cited

OTHER PUBLICATIONS

European Patent Office, "Termination of opposition proceedings of patent No. 13761575.3-1113/2825129 with maintenance of the patent", *in re Opposition by Pronovem Luxembourg s.a. to European Application No. 13761575.3*, Jan. 17, 2020, 1 page.

European Patent Office, "Maintenance of the patent with the documents specified in final decision", *in re Opposition by Pronovem Luxembourg s.a. to European Application No. 13761575.3*, Oct. 25, 2019, 1 page.

European Patent Office, "Minutes of Oral Hearing-Decision on Opposition", *in re Opposition by Pronovem Luxembourg s.a. to European Application No. 13761575.3*, Patent No. EP-B-2 825 129, Jun. 4, 2019, 145 pages.

European Patent Office, "Information re the result of oral proceedings", *in re Opposition by Pronovem Luxembourg s.a. to European Application No. 13761575.3*, Mar. 18, 2019, 24 pages.

Terumo Corporation (Propietor), "Observations by Proprietor to Notice of Opposition", *in re Opposition by Pronovem Luxembourg s.a. to European Patent No. EP2825129*, Jan. 18, 2019, 80 pages.

European Patent Office, "Summons to attend oral proceedings", *in re Opposition by Pronovem Luxembourg s.a. to European Application No. 13761575.3*, Aug. 8, 2018, 17 pages.

Microvention, Inc. (Propietor), "Reply by Proprietor to Notice of Opposition", *in re Opposition by Pronovem Luxembourg s.a. to European Patent No. EP2825129*, Mar. 23, 2018, 26 pages.

Pronovem Luxembourg s.a. (OPPONENT), "Notice of Opposition to a European Patent", *in re Opposition by Pronoverm Luxumbourg s.a. to European Application No. 13761575.3*, Patent No. EP2825129B1, Jan. 18, 2017, 16 pages.

European Patent Office, Notice of Opposition dated Oct. 18, 2017 in European Patent No. EP 2 825 129 B1, 14 pages.

Australian Patent Office, Second Examination Report dated Dec. 24, 2016 in Australian Patent Application No. 2011341445, 3 pages.

European Patent Office, Office Action dated Oct. 28, 2016 in European Patent Application No. EP11848071, 6 pages.

European Patent Office, Third Party Observation dated Oct. 28, 2016 in European Patent Application No. EP11848071, 3 pages.

Chinese Patent Office, First Office Action dated May 20, 2016 in Chinese Patent Application No. 201180067440.3, 22 pages.

Australian Patent Office, Third Examination Report dated May 20, 2016 in Australian Patent Application No. 2011341445, 4 pages.

Japanese Patent Office, Penultimate Office Action dated May 4, 2016 in Japanese Patent Application No. 2013-544546, 10 pages.

Chinese Patent Office, Second Office Action dated Apr. 6, 2016 in Chinese Patent Application No. 201180067440.3, 11 pages.

Japanese Patent Office, First Office Action dated Oct. 8, 2014 in Japanese Patent Application No. 2013-544546, 15 pages.

European Patent Office, Extended European Report dated Sep. 12, 2013 in European Patent Application No. EP11848071.4-1455, 7 pages.

European Patent Office, Supplementary Search Report dated Sep. 12, 2013 in European Patent Application No. EP11848071, 7 pages.

WIPO, U.S. International Preliminary Examining Authority, International Preliminary Report on Patentability dated Jun. 26, 2013 in International Patent Application No. PCT/US2011/063330, 6 pages.

WIPO, U.S. International Search Authority, International Search Report and Written Opinion dated May 25, 2012 in International Application No. PCT/US 11/63330, 8 pages.

WIPO, U.S. International Search Authority, International Search Report and Written Opinion dated May 25, 2012 in International Patent Application No. PCT/US2011/063330, 8 pages.

WIPO, U.S. International Search Authority, International Search Report and Written Opinion dated Mar. 7, 2011 in International Patent Application No. PCT/US2010/061627, 9 pages.

Henry, Michel et al., "Treatment of Renal Artery Aneurysm With the Multilayer Stent", J Endovasc Ther 2008, 15:231-236, 6 pages.

Han, Y.M. et al., "Flared Polyurethane-covered Self-expandable Nitinol Stent for Malignant Biliary Obstruction," *J Vasc Interv Radiol*, Oct. 2003; 14 (10): pp. 1291-1301.

Lieber, B.B. et al., "Alteration of Hemodynamics in Aneurysm Models by Stenting: Influence of Stent Porosity," *Annals of Biomedical Engineering*, 1997, vol. 25, pp. 460-469.

Balt Extrusion, Montmorency, Francy, "LEO+," Intracranial self expandable stent and delivery system, product page.

\* cited by examiner

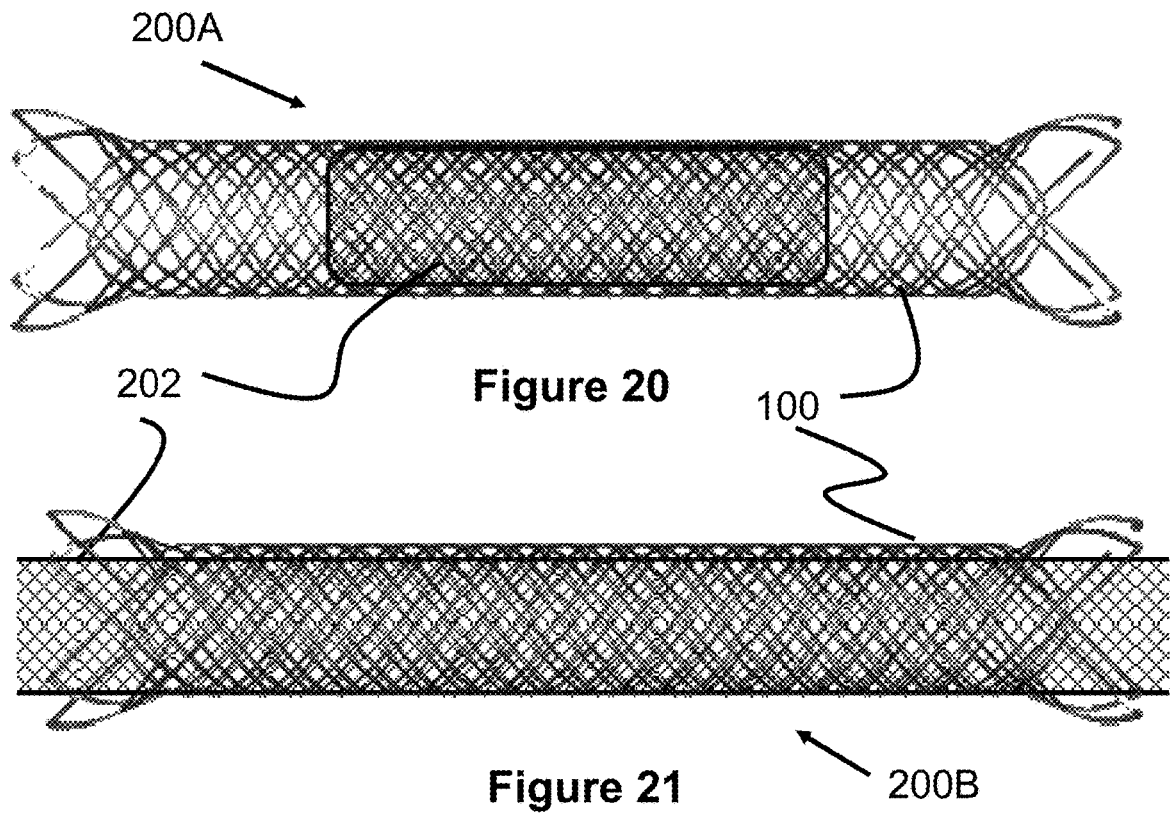
Figure 20
Figure 21
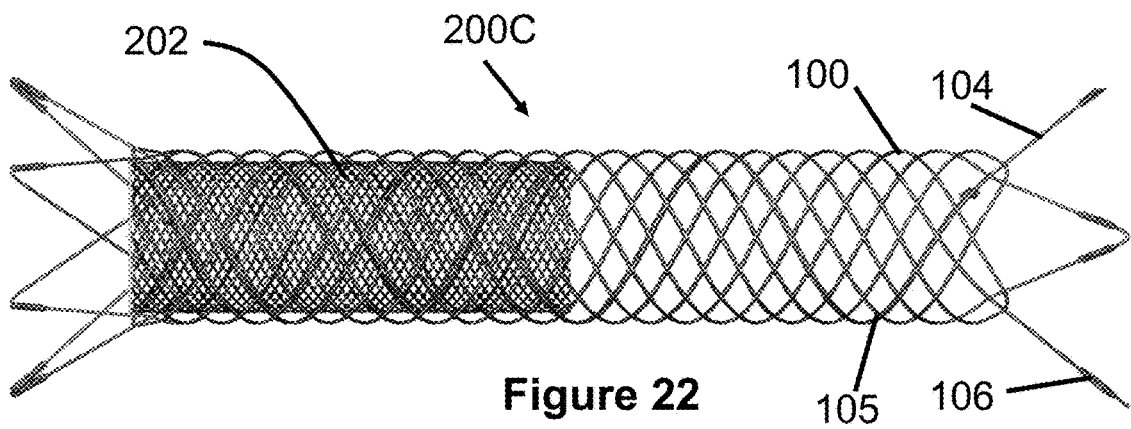
Figure 22

STENT

RELATED APPLICATIONS

This application is a continuation of and claims priority to U.S. patent application Ser. No. 17/244,499 filed Apr. 29, 2021 entitled Stent, which is a continuation of and claims priority to U.S. patent application Ser. No. 16/590,252 filed Oct. 1, 2019 entitled Stent, which is a continuation of and claims priority to U.S. patent application Ser. No. 15/784,052 filed Oct. 13, 2017 entitled Stent (now U.S. Pat. No. 10,463,515 issued Nov. 5, 2019), which is a continuation of and claims priority to U.S. patent application Ser. No. 13/311,430 filed Dec. 5, 2011 entitled Stent (now U.S. Pat. No. 9,867,725 issued Jan. 16, 2018), which claims benefit of and priority to U.S. Provisional Patent Application Ser. No. 61/422,604 filed Dec. 13, 2010 entitled Stent; to U.S. Provisional Patent Application Ser. No. 61/425,175 filed Dec. 20, 2010 entitled Polymer Stent And Method Of Manufacture; to U.S. Provisional Patent Application Ser. No. 61/427,773 filed Dec. 28, 2010 entitled Polymer Stent And Method Of Manufacture 2; and which is a continuation-in-part of U.S. Nonprovisional patent application Ser. No. 13/003,277 filed Aug. 23, 2020 entitled Stent, which is the U.S. National Phase of and claims priority to International Patent Application No. PCT/US2010/061627 filed Dec. 21, 2010 entitled Stent; all of which are hereby incorporated herein by reference in their entireties.

BACKGROUND OF THE INVENTION

The present invention relates to devices for the treatment of body cavities, such as the embolization of vascular aneurysms and the like, and methods for making and using such devices.

The occlusion of body cavities, blood vessels, and other lumina by embolization is desired in a number of clinical situations. For example, the occlusion of fallopian tubes for the purposes of sterilization, and the occlusive repair of cardiac defects, such as a patent foramen ovale, patent ductus arteriosis, and left atrial appendage, and atrial septal defects. The function of an occlusion device in such situations is to substantially block or inhibit the flow of bodily fluids into or through the cavity, lumen, vessel, space, or defect for the therapeutic benefit of the patient.

The embolization of blood vessels is also desired to repair a number of vascular abnormalities. For example, vascular embolization has been used to control vascular bleeding, to occlude the blood supply to tumors, and to occlude vascular aneurysms, particularly intracranial aneurysms.

In recent years, vascular embolization for the treatment of aneurysms has received much attention. Several different treatment modalities have been shown in the prior art. One approach that has shown promise is the use of thrombogenic microcoils. These microcoils may be made of biocompatible metal alloy(s) (typically a radio-opaque material such as platinum or tungsten) or a suitable polymer. Examples of microcoils are disclosed in the following patents: U.S. Pat. No. 4,994,069—Ritchart et al.; U.S. Pat. No. 5,133,731—Butler et al.; U.S. Pat. No. 5,226,911—Chee et al.; U.S. Pat. No. 5,312,415—Palermo; U.S. Pat. No. 5,382,259—Phelps et al.; U.S. Pat. No. 5,382,260—Dormandy, Jr. et al.; U.S. Pat. No. 5,476,472—Dormandy, Jr. et al.; U.S. Pat. No. 5,578,074—Mirigian; U.S. Pat. No. 5,582,619—Ken; U.S. Pat. No. 5,624,461—Mariant; U.S. Pat. No. 5,645,558—Horton; U.S. Pat. No. 5,658,308—Snyder; and U.S. Pat. No. 5,718,711—Berenstein et al.; all of which are hereby incorporated by reference.

Stents have also been recently used to treat aneurysms. For example, as seen in U.S. Pat. No. 5,951,599—McCrory and U.S. Pub. No. 2002/0169473—Sepetka et al., the contents of which are incorporated by reference, a stent can be used to reinforce the vessel wall around the aneurysm while microcoils or other embolic material are advanced into the aneurysm. In another example seen in U.S. Pub. No. 2006/0206201—Garcia et al. and also incorporated by reference, a densely woven stent is placed over the mouth of the aneurysm which reduces blood flow through the aneurysm's interior and ultimately results in thrombosis.

SUMMARY OF THE INVENTION

In one embodiment according to the present invention, a stent is described having a generally cylindrical body formed from a single woven nitinol wire. The distal and proximal ends of the stent include a plurality of loops, some of which include marker members used for visualizing the position of the stent.

In another embodiment according to the present invention, a delivery device is described, having an outer catheter member and an inner pusher member disposed in a passage of the catheter. The distal end of the pusher member includes a distal and proximal marker band that is raised above the adjacent portions of the pusher member body. The previously described stent can be compressed over the distal marker band such that the stent's proximal loops and proximal marker members are disposed between the distal and proximal marker bands on the pusher member.

In one example, the delivery device can be used to deliver the previously described stent over an opening of an aneurysm. The aneurysm is preferably first filled with microcoils or embolic material either before or after delivery of the stent.

In another embodiment according to the present invention, a dual layer stent is described having an outer anchoring stent similar to the previously described stent and a discrete inner mesh layer formed from a plurality of woven members. The proximal end of the outer stent and the inner stent are connected together by connecting members or crimping, allowing the remaining portions of the outer anchoring stent and inner mesh layer to independently change in length as each begins to expand in diameter. Alternately, the inner mesh layer may only extend along a portion of the length of outer stent and may be symmetrically or asymmetrically positioned between the out stent's distal and proximal ends.

In one example, the dual layer stent can be delivered over the opening of an aneurysm to modify the flow of blood that enters the aneurysm. As the blood flow into the aneurysm becomes stagnant, a thrombosis forms to block up the interior aneurysm space.

In another embodiment according to the present invention, a single or dual layer stent can be created by polymerizing a prepolymer liquid inside a tube, syringe or similar structure. Patterns can be created in the polymer structure via a pre-patterned mandrel on which the polymer structure is polymerized or by cutting the polymer structure after polymerization.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 20 illustrates a dual layer stent according to the present invention having a shortened flow-diverting layer;

FIG. 21 illustrates a dual layer stent according to the present invention having an elongated flow-diverting layer;

FIG. 22 illustrates a dual layer stent according to the present invention having an asymmetrically positioned flow-diverting layer;

DESCRIPTION OF EMBODIMENTS

Figure 1:
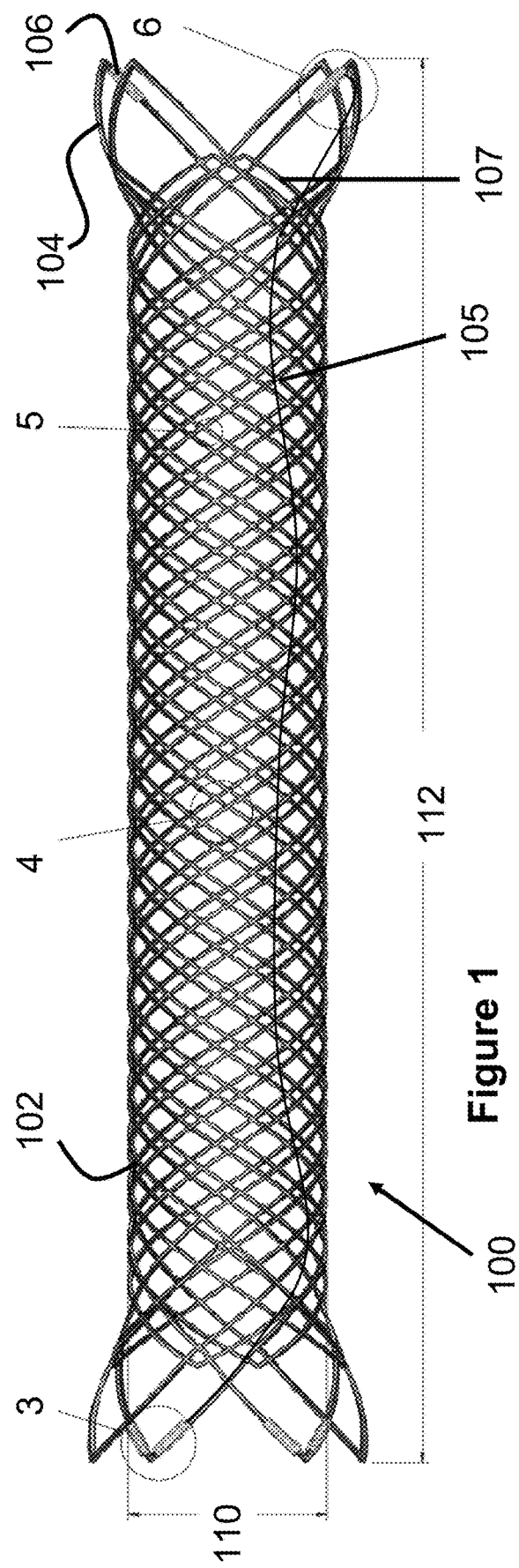
FIG. 1 illustrates a side view of a stent according to a preferred embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 illustrates a stent 100 according to a preferred embodiment of the present invention. The stent 100 is woven or braided together from a single wire 102 to form a generally cylindrical shape with a plurality of loops 104 around the perimeter of both ends of the stent 100.

Figure 5:
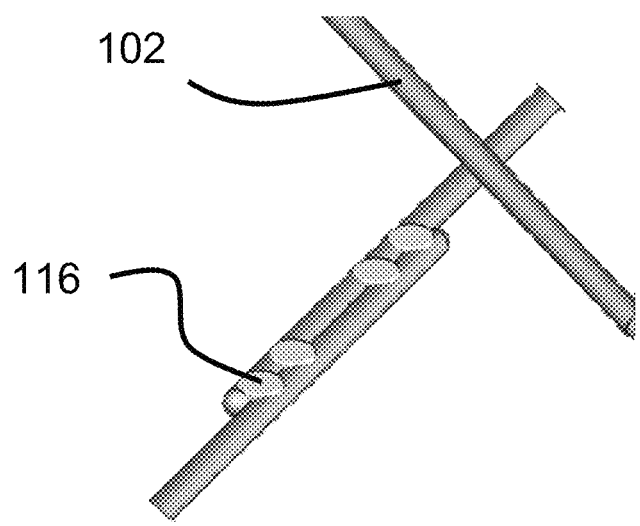
FIG. 5 illustrates a magnified view of area 5 in FIG. 1.

As seen in area 5 in FIG. 1 and in FIG. 5, the ends of the single wire 102 can be connected to each other via welding (see welded region 116), bonding agents or a similar adhesive mechanism. Once the ends are welded or bonded, the wire 102 has no "free" ends.

Each of the loops 104 may contain one or more coil members 106. Preferably, the coil members 106 are disposed around the wire 102 of the loops 104 which, as discussed in greater detail below, denote the proximal and distal ends of the stent 100. Additionally, these coil members 106 may provide additional anchoring force within a delivery device as described in greater detail below.

In one example, a distal end of the stent 100 includes at least two loops 104 with two coil members 106 each and a proximal end of the stent 100 includes at least two loops 104 with one coil member 106 each. However, it should be understood that the stent 100 can include any number of coil members 106 on any number of loops 104.

Preferably, these coil members 106 are positioned near a center area of the loop 104, such that when the stent 100 is in a collapsed state, the coil members 106 are positioned near the very distal or very proximal end of the stent 100.

Figure 3:
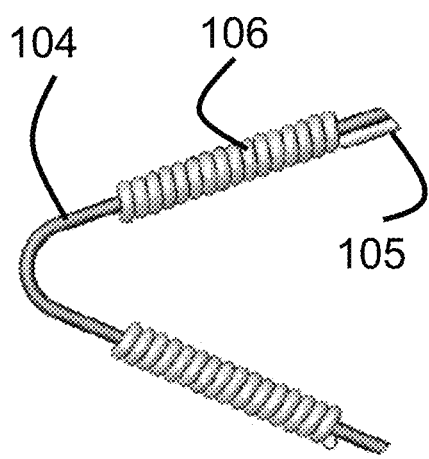
FIG. 3 illustrates a magnified view of area 3 in FIG. 1.
Figure 4:
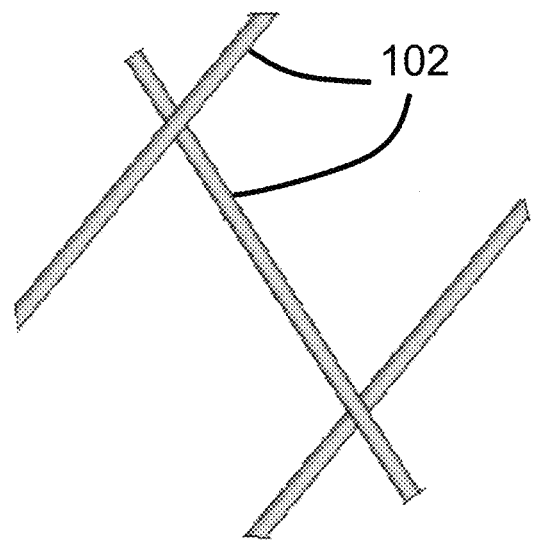
FIG. 4 illustrates a magnified view of area 4 in FIG. 1.
Figure 6:
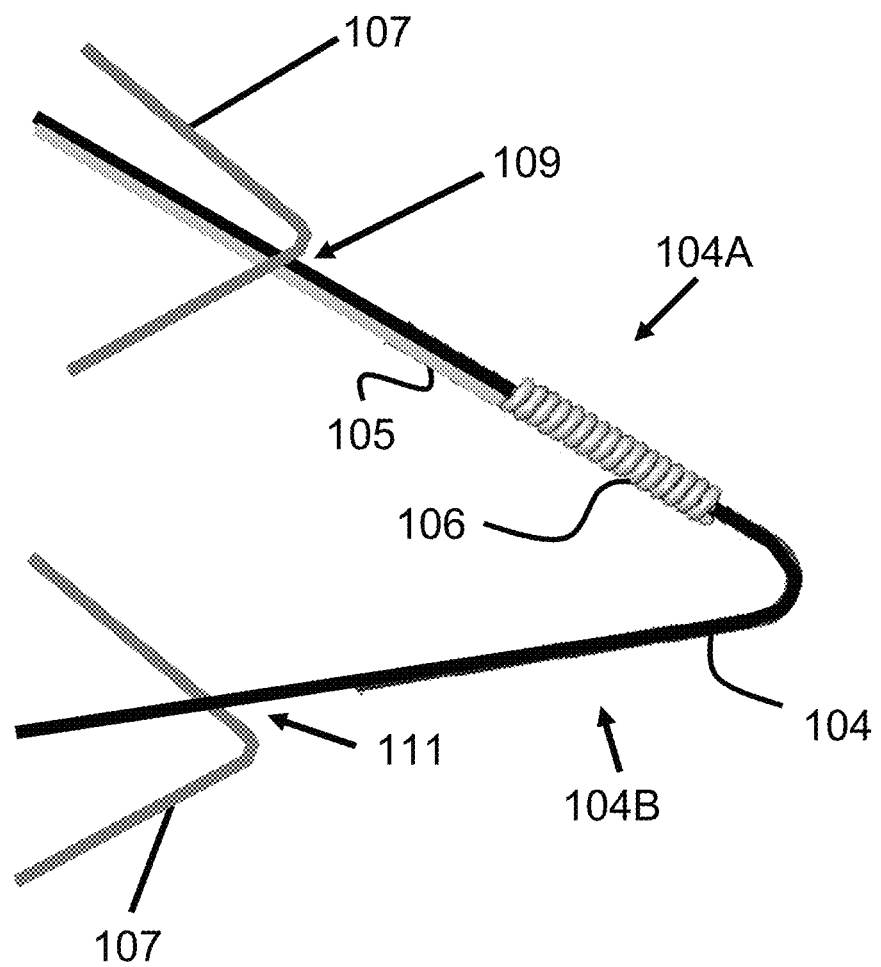
FIG. 6 illustrates a magnified view of area 6 in FIG. 1.

Preferably, each coil member 106 is composed of a wire 105 wound around a portion of the loop 104. Each coil member 106 can be composed of a discrete wire 105 (as seen in FIG. 3) or a single wire 105 can form multiple coil members 106 (as seen in FIGS. 1, 3 and 6). In the present preferred embodiment, some coil members 106 are composed of discrete sections of wire 105 while other coil members 106 on either end are formed from the same, continuous wire 105. As seen in FIG. 1, the wire 105 can connected to coil members 106 on each end of the stent 100 by being located within the inner portion or lumen of the stent 100. Alternately, the wire 105 may be woven into the wires 102 of the stent 100.

Preferably, the wire 105 of the coil members 106 is composed of a radiopaque material such as tantalum or platinum. The wire 105 preferably has a diameter of about 0.00225".

Alternately, the coil members 106 may be a radiopaque sleeve that is disposed on and adhered to the loop 104.

In one embodiment, the loops 104 on the proximal end of the stent 100 have one coil 106 on each side of the loop 104 (as seen in FIG. 3) while the distal end of the stent 100 includes only one coil 106 on one side of each loop 104 (as seen in FIG. 6).

Preferably, the weaving pattern of the stent 100 prevents the distal coils 106 from being exposed or "sticking up" from an outer diameter of the stent 100 during retraction. Hence, if the user decides to retract the stent 100 back into the catheter for repositioning and redeployment, the distal coils 106 will not catch or contact the distal edge of the catheter, thereby minimizing damage to the stent 100 that might otherwise occur during retraction.

One specific technique for minimizing the exposure of the distal coils 106 during retraction is to weave the stent 100 such that portions of the wire 102 overlap (i.e., are positioned at a greater outer diameter position) than the side of the loop 104 with coil 106. As seen in FIG. 6, some smaller, minor loops 107 are woven to overlap a first side 104A of the loop 104 that includes the coil 106 (see location 109) while other minor loops 107 are woven underneath a second side 104B of the loop 104 (see location 111).

As a user retracts the stent 100 back into the catheter, the minor loops 107 move inward (i.e., towards the center of the stent's passage) as the stent 100 compresses in diameter, thereby inwardly pressing on the first side 104A of the loop 104. In this respect, the minor loops 107 exert inward or compressive force on the first side 104A of the loop 104. This configuration ensures that the first side 104A of the loop 104 and therefore the coil 106 is not positioned at an outermost diameter of the stent 100 during retraction and therefore reduces the likelihood of the coils 106 of catching or hooking on to the distal end of the deployment catheter.

Figure 2:
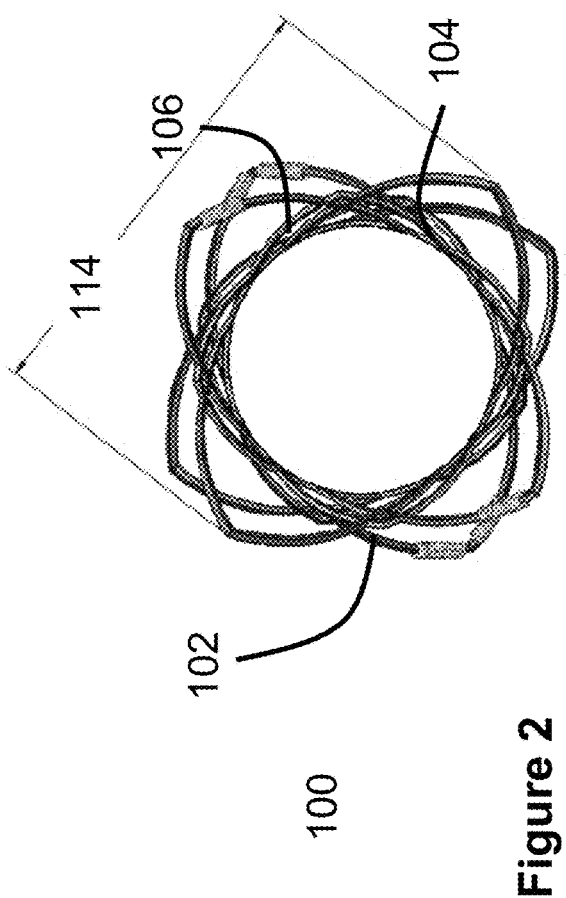
FIG. 2 illustrates a front view of the stent of FIG. 1.

As seen best in FIG. 1 and FIG. 2, the loops 104 are flared or biased to an outer diameter 114 when fully expanded relative to the diameter of the main body of stent 100. These loops 104 can also expand to a diameter that is even with or smaller than that of the main body.

Figure 9:
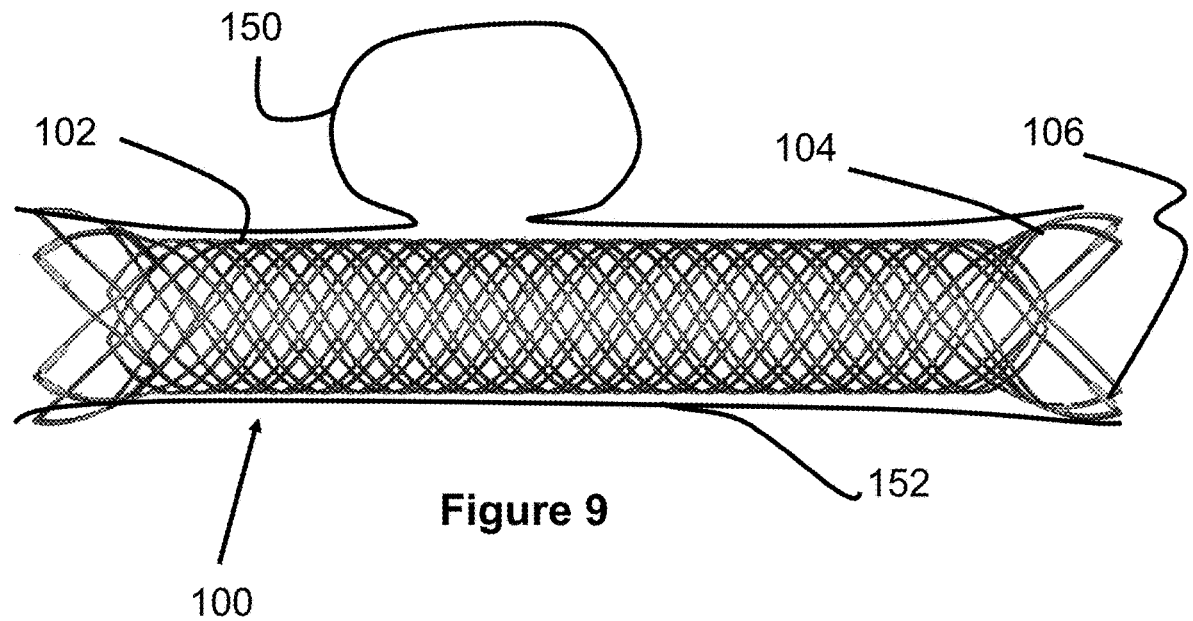
FIG. 9 illustrates the stent of FIG. 1 positioned over the opening of an aneurysm.

The stent 100 preferably has a diameter 110 sized for a vessel 152 in the human body, as seen in FIG. 9. More preferably, the diameter 110 is between about 2 mm and 10 mm. The length of the stent 100 is preferably sized to extend beyond the mouth of an aneurysm 150 as also seen in FIG. 9. More preferably, the length of the stent 100 is between about 5 mm and 100 mm.

Figure 7:
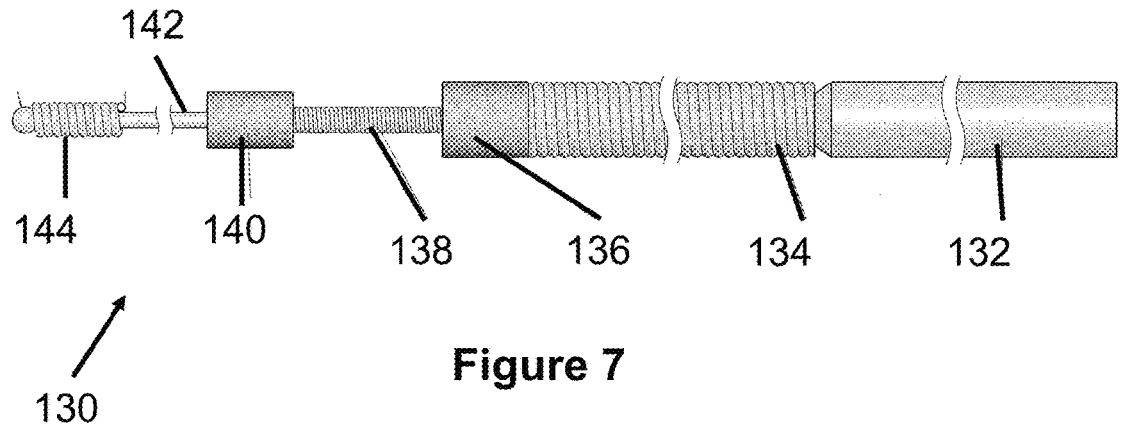
FIG. 7 illustrates a side view of a pusher member according to a preferred embodiment of the present invention.
Figure 8:
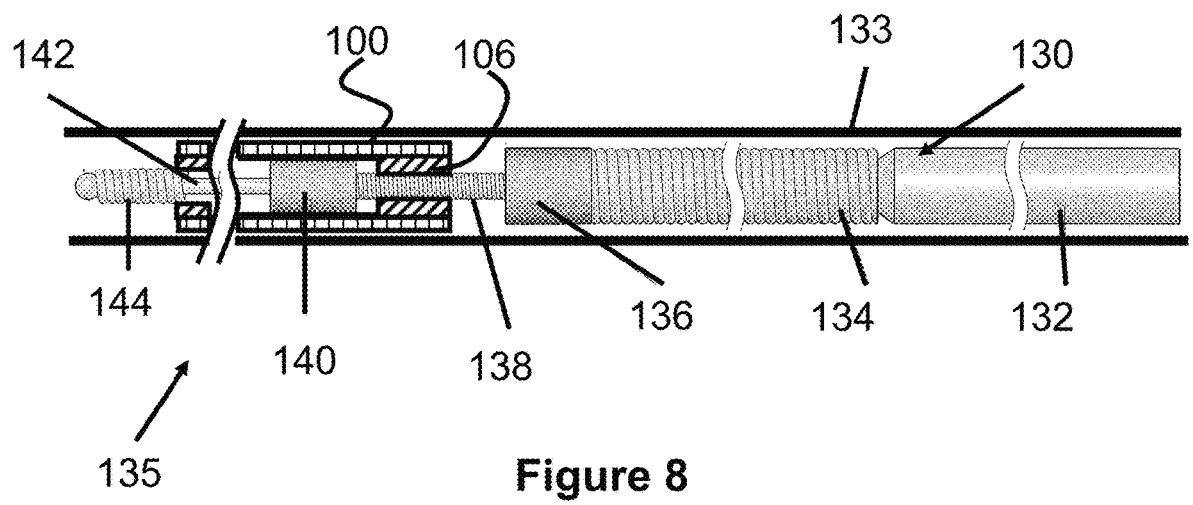
FIG. 8 illustrates a partial cross sectional view of the pusher member of FIG. 7 having the stent of FIG. 1 compressed over its distal end and being positioned in a catheter.

FIGS. 7 and 8 illustrate a delivery system 135 according to the present invention which can be used to deliver the stent 100. A catheter or sheath 133 is positioned over a delivery pusher 130, maintaining the stent 100 in its compressed position. Once the distal end of the sheath 133 has achieved a desired target location (i.e., adjacent an aneurysm 150), the sheath 133 can be retracted to release the stent 100.

The delivery pusher 130 is preferably composed of a core member 132, which tapers in diameter near its distal end (made from nitinol). A proximal area of the tapered end of the core member 132 includes a larger diameter first wire coil 134 that is preferably made from stainless steel and welded or soldered in place on the core member 132. Distal to the coiled wire is a first marker band 136 that is fixed to the core member 132 and preferably made from a radiopaque material such as platinum.

A smaller diameter second wire coil 138 is located distal to the marker band 136 and is preferably made from stainless steel or plastic sleeve. A second marker band 140 is located distal to the second wire coil 138 and is also preferably made from a radiopaque material such as platinum. Distal to the second marker band 140 is a narrow, exposed section 142 of the core member 132. Finally, a coiled distal tip member 144 is disposed on the distal end of the core member 132 and is preferably composed of a radiopaque material such as platinum or tantalum.

In one example, the inner diameter of the sheath 133 is about 0.027" and about 1 meter in length. The delivery pusher 130 is also about 2 meters in length. The sections of the delivery pusher 130 preferably have the following diameters: the proximal region of the core member 132 is about 0.0180 inch, the first wire coil 134 is about 0.0180 inch, the first marker band 136 is about 0.0175 inch, the second wire coil 138 is about 0.0050 inch, the second marker band 140 is about 0.0140 inch, the distal core member section 142 is about 0.003 inch, and the distal tip member 144 is about 0.0100 inch. The sections of the delivery pusher 130 preferably have the following lengths: the proximal region of the core member 132 is about 1 meter, the first wire coil 134 is about 45 cm, the first marker band 136 is about 0.020 inch, the second wire coil 138 is about 0.065 inch, the second marker band 140 is about 0.020 inch the distal core member section 142 is about 10 cm, and the distal tip member 144 is about 1 cm.

As seen in FIG. 8, the stent 100 is compressed over the distal end of the delivery pusher 130 such that the coil members 106 on the proximal end of the stent 100 are positioned between the first marker band 136 and the second marker band 140. Preferably, the proximal coil members 106 are not in contact with either marker band 136 or 140 and are maintained via frictional forces between the sheath 133 and the second coiled area 138.

When the distal end of the delivery pusher has reached an area adjacent a desired target location (e.g., near an aneurysm), the sheath 133 is retracted proximally relative to the delivery pusher 130. As the sheath 133 exposes the stent 100, the stent 100 expands against the walls of the vessel 152, as seen in FIG. 9.

The stent 100 can also be retracted (if it was not fully deployed/released) by retracting the pusher 130 in a proximal direction, thereby causing the marker band 140 to contact the proximal marker bands 106, pulling the stent 100 back into the sheath 133.

In one exemplary use, the stent 100 can be delivered over the opening of an aneurysm 150 after embolic devices or material, such as embolic coils, have been delivered within the aneurysm 150. In this respect, the stent 100 helps prevent the treatment devices from pushing out of the aneurysm 150 and causing complications or reducing efficacy of the treatment.

In one example, the wire 102 is composed of a shape-memory elastic material such as nitinol between about 0.001 inch and 0.010 inch in diameter.

The wire 102 may also vary in diameter over the length of the stent 100. For example, the diameter of the wire 102 near the proximal and distal ends may be thicker than that of the middle portion of the stent 100. In another example, the proximal and distal ends may be thinner than the middle portion. In another example, the diameter of the wire 102 may alternate between larger and smaller diameters along the length of the stent 100. In yet another example, the diameter of the wire 102 may gradually increase or decrease along the length of the stent 100. In yet another example, the loops 104 may be composed of wire 102 having a larger or smaller diameter than that of the wire 102 comprising the main body of the stent 100. In a more detailed example, the diameter of the wire 102 of the loops 104 may be about 0.003 inch while the wire 102 of the body of the stent 100 may be about 0.002 inch.

In yet another example, select areas of the wire 102 may have a reduced thickness where the wire 102 may cross over another section in a compressed and/or expanded configuration of the stent 100. In this respect, the thickness of the stent 100 can be effectively reduced in certain configurations. For example, if sections of the wire 102 were reduced at areas where the wire 102 overlapped when in a compressed configuration, the overall profile or thickness of the stent 100 can be reduced, allowing the stent 100 to potentially fit into a smaller delivery catheter.

This variation in diameter of the wire 102 can be achieved by electropolishing, etching or otherwise reducing portions of the assembled stent 100 to cause a diameter reduction. Alternately, regions of the wire 102 can be reduced prior to being wound or woven into the shape of the stent 100. In this respect, a desired weaving pattern can be determined, the desired post-weaving, reduced-diameter regions can be calculated and reduced, and finally the stent 100 can be woven with the modified wire 102.

In another variation, the pre-woven wire 102 can be tapered along a single direction and woven together to form the stent 100.

Figure 10:
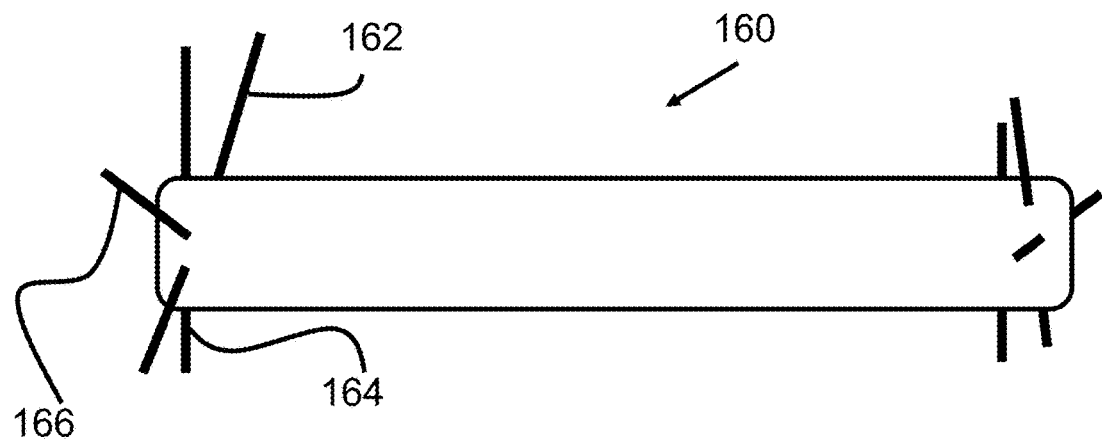
FIG. 10 illustrates a side view of a mandrel according to the present invention that can be used to create the stent of FIG. 1.

In one exemplary preparation, a 0.0035 inch diameter nitinol wire is wound or woven over a mandrel 160. As seen in FIG. 10, the mandrel 160 may have three pins 162, 164, 166 extending through each end, such that a portion of each end of each pin extends out from the body of the mandrel 160. The wire 102 begins at one pin, and then is wound 3.0625 revolutions clockwise around the body of the mandrel 160. The wire 102 is bent around a nearby pin, then wound 3.0625 revolutions clockwise back towards the other side of the mandrel 160, passing over and under the previously wound section of wire 102. This process is repeated until eight loops are formed on each end.

In another example, the mandrel 160 may have 8 pins and the wire 102 is wound 2.375 revolutions. In another example, the mandrel 160 may have 16 pins and the wire 102 is wound 3.0625 revolutions. In yet another example, the mandrel may have between 8 and 16 pins and is wound between 2.375 and 3.0625 revolutions.

Once wound, the stent 100 is heat-set on the mandrel 160, for example, at about 500° C. for about 10 minutes. The two free ends of the nitinol wire can be laser welded together and electro-polished such that the final wire diameter is about 0.0023 inch.

Finally, the radiopaque wire 105 of about 0.00225 inch in diameter is wound onto different areas of the stent loops 104, forming coil members 106. Preferably, the wire 105 is wound for about 0.04 inch in length to create each coil member 106.

In another embodiment, the stent 100 can be formed from a plurality of discrete wires instead of a single wire 102. The ends of this plurality of wires can be left free or can be welded, adhered or fused together for form loops 104. In another embodiment, the stent 100 can be formed by laser cutting, etching, machining or any other known fabrications methods.

The wire 102 is preferably composed of a shape memory metal such as Nitinol. Optionally, this shape memory metal can include a variety of different therapeutic coatings or a hydrogel coating that swells or expands when exposed to blood. The wire 102 can also be composed of a biocompatible polymer material (e.g., PET) or from a hydrogel material.

Figure 11:
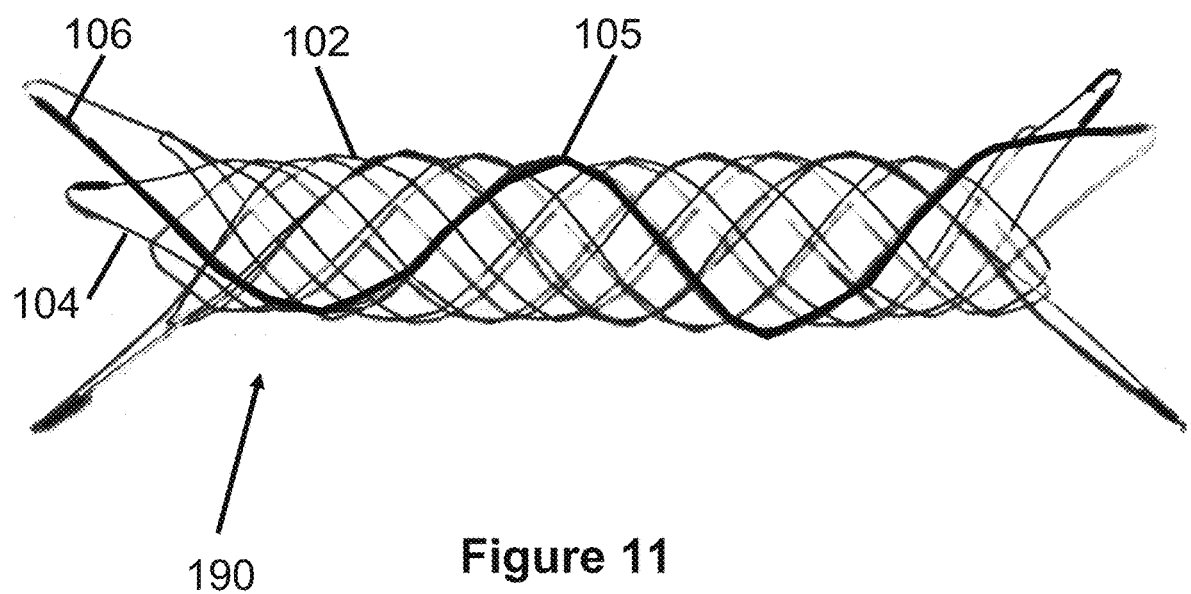
FIG. 11 illustrates a side view of a stent according to a preferred embodiment of the present invention.

FIG. 11 illustrates an embodiment of a stent 190 that is similar to the previously described stent 100, except that each end of the stent 190 includes three loops 104 instead of the four loops 104 of the previous stent 100. Additionally, the radiopaque wire 105 that form each of the coils 106 is also preferably woven into the stent 190, connecting at least some of the coils 104 on each end of the stent 190. Finally, the wire 102 is woven back and forth about 12 times along the length of the stent 190.

Figure 12:
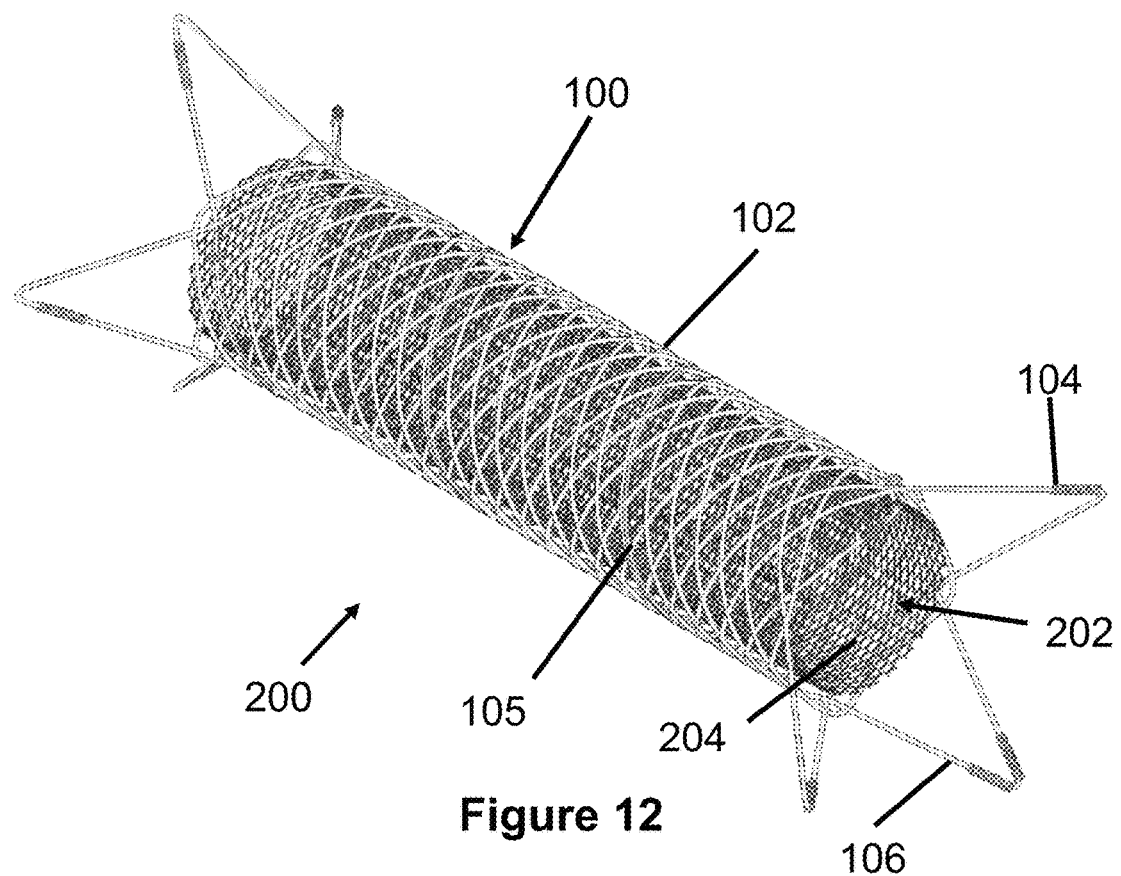
FIGS. 12-14 illustrate various views of a dual layer stent according to a preferred embodiment of the present invention.

FIG. 12 illustrates a preferred embodiment of a dual layer stent 200 according to the present invention. Generally, the dual layer stent 200 includes an outer anchoring stent 100 that is similar to the previously described stent 100 seen in FIGS. 1-9. The dual layer stent 200 also includes an inner flow-diverting layer 202 that is disposed within the inner lumen or passage of the anchoring stent 100.

Often, stents with relatively small wires do not provide adequate expansile forces and therefore do not reliably maintain their position at a target location. Additionally, prior art woven stents created with many wires can have free ends that can poke or damage a patient's vessel. In contrast, larger wires are difficult to weave tightly enough (i.e., large spaces between adjacent wires) to modify blood flow at a desired location. The stent 200 seeks to overcome these disadvantages by including both the larger wire braid anchoring stent 100 to provide a desired anchoring force and the smaller wire braid flow-diverting layer 202 to divert blood.

In one example, the flow-diverting layer 202 is composed of at least 32 wires 204 that are between about 0.0005 to about 0.002 inch in diameter and made from a memory elastic material such as nitinol. These wires 204 are woven or braided together in a tubular shape having a pore size less than 0.010 inch. Preferably, this braiding is achieved with a braiding machine, which is known in the art and can braid the wires 204 in a regular pattern such as a diamond shaped pattern.

The flow-diverting layer 202 can have areas of its wire 204 that have a reduced diameter, similar to the patterns and techniques previously described with regard to the wire 102 of the stent 100. Additionally, the flow-diverting layer 202 can be formed by laser cutting or etching a thin tube.

In the present example, the distal and proximal ends of the flow-diverting layer 202 are perpendicular relative to the length of the layer 202. However, these ends may also be angled relatively to the length of layer 202 in a matching, opposite or irregular angular configuration.

Figure 13:
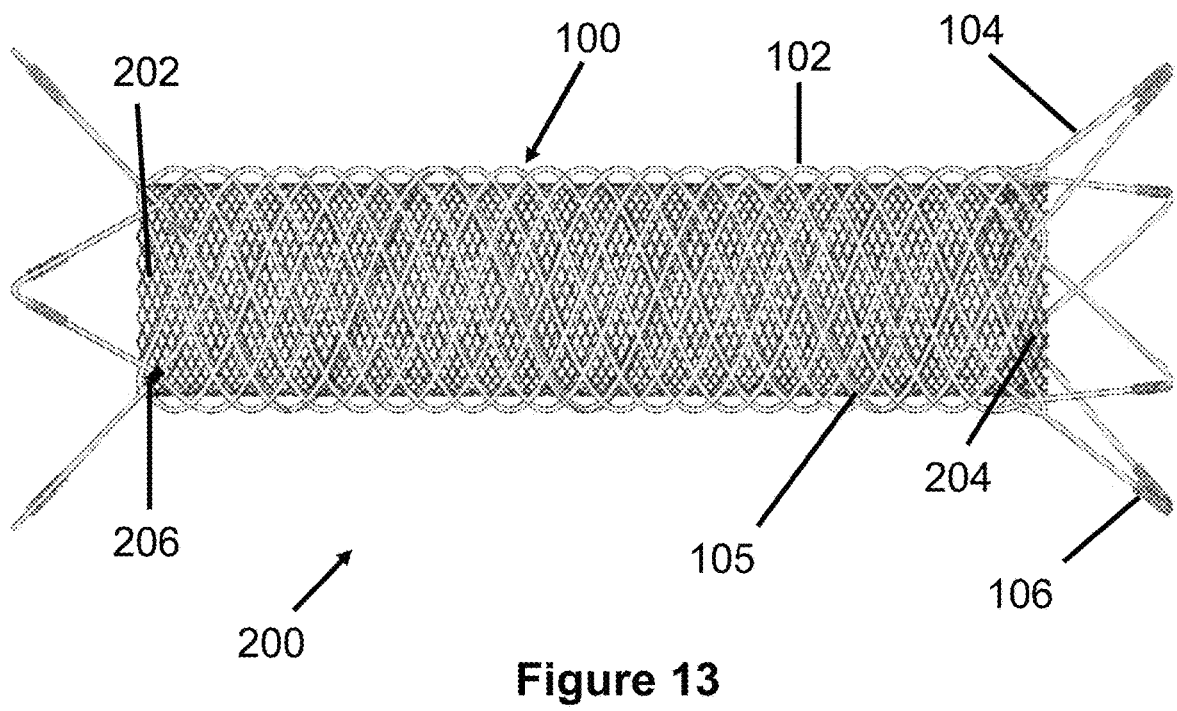
Figure 14:
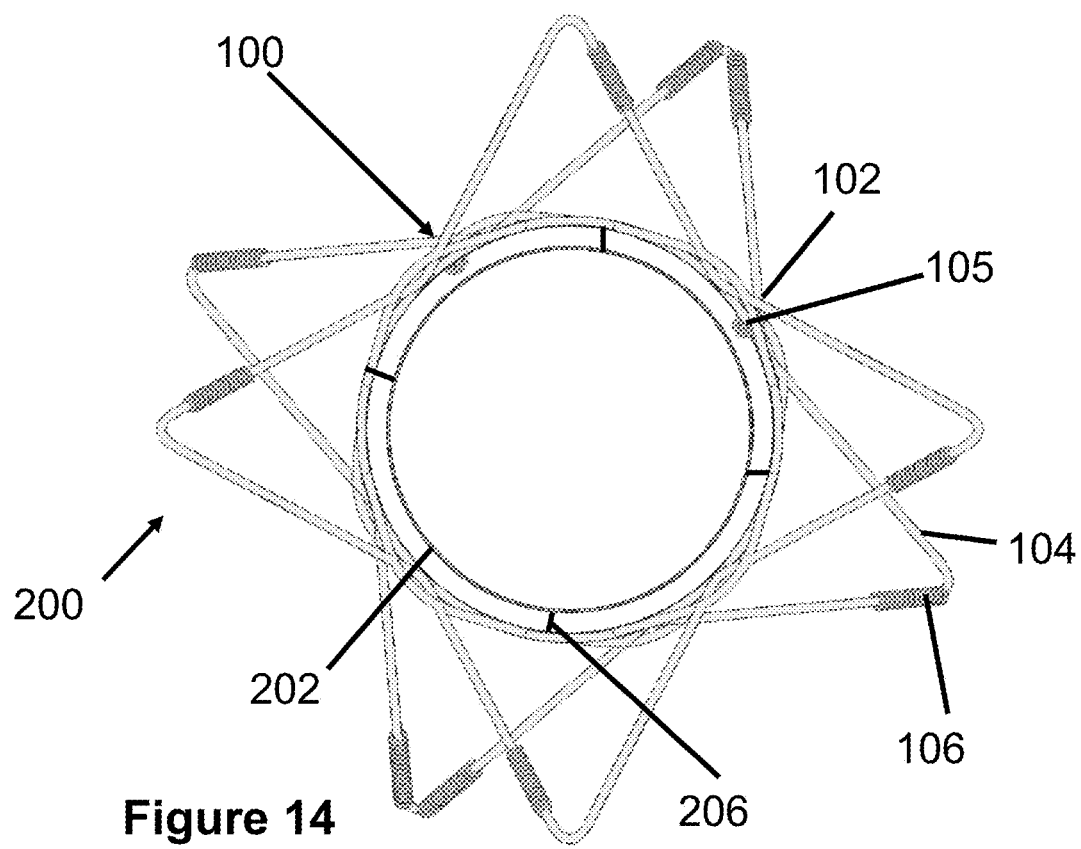

As best seen in FIGS. 13 and 14, the proximal end of the dual layer stent 200 includes a plurality of attachment members 206 that connect the anchoring stent 100 with the flow-diverting layer 202. The attachment members 206 can be composed of tantalum wire (in this case is 0.001" dia.) and can be attached to portions of wire 102 and wire 202. In another embodiment, the proximal end of the flow-diverting layer 202 can be crimped on to the wires 102 of the anchoring stent 100. In another embodiment, portions of the stent 100 and flow-diverting layer can be woven through each other for attachment purposes. In yet another embodiment, the stent 100 can be formed with eye-loops (e.g., formed via laser cutting or etching) or similar features sized to allow wires 202 to be woven through for attachment purposes.

Since the anchoring stent 100 and the flow-diverting layer 202 may have different weave patterns or weave densities, both will shorten in length at different rates as their diameter expands. In this respect, the attachment members 206 are preferably located at or near the proximal end of the anchoring stent 100 and the flow-diverting layer 202 as oriented in the delivery device (i.e., on the end opposite the distal tip member 144). Hence, as the stent 200 is deployed, both the anchoring stent 100 and the flow-diverting layer 202 can decrease in length (or increase if retracting the stent 200 back into a delivery device), yet remain attached to each other. Alternately, attachment members 206 can be positioned at one or more locations along the length of the dual layer stent 200 (e.g., at the distal end, both ends, the middle, or at both ends and the middle region).

In one exemplary embodiment of the stent 200, a flow-diverting layer 202 comprises 48 wires with a density of about 145 ppi and fully expands to a diameter of about 3.9 mm. An outer stent 100 comprises a single wire wound in a 2.5 revolution winding pattern and fully expands to a diameter of about 4.5 mm. When both layers 100 and 202 are fully expanded, the lengths are about 17 mm and 13 mm respectively. When both layers 100 and 202 are compressed on a 0.027 inch region of a delivery device, their lengths are about 44 mm and 37 mm respectively. When both layers 100 and 202 are expanded within a 3.75 mm vessel, their lengths are about 33 mm and 21 mm respectively.

In one preferred embodiment of the dual layer stent 200, the flow-diverting layer 202 is composed of wires 204 having a diameter between about 0.0005 inch and about 0.0018 inch and the wires 102 of the stent 100 have a diameter between about 0.0018 inch and about 0.0050 inch. Therefore, the minimum preferred ratio between the diameter of the wire 102 and wire 204 is about 0.0018 to 0.0018 inch respectively (or about a 1:1 ratio) and the maximum preferred ratio is about 0.0050/0.0005 inch (or about a 10:1).

It should be noted that the dual layer stent 200 can produce a larger amount of radial force (defined as the radial force exerted at about 50% radial compression of a stent) than either the stent 100 or flow diverting layer 200 alone. This higher radial force allows the dual layer stent 200 to have improved deployment and anchoring characteristics. In one exemplary test of a dual layer stent embodiment, the outer stent 100 alone had an average radial force of about 0.13 N, the flow diverting layer 202 alone had an average radial force of about 0.05 N and the dual layer stent 200 had an average radial force of about 0.26 N. In other words, the average radial force of the stent 200 was greater than or equal to that of the flow diverting layer 202 and the stent 100 combined.

It should be noted that the porosity (i.e., the percentage of open space to non-open space) in the flow-diverting layer 202 changes as it radially expands. In this respect, a desired porosity or pore size can be controlled by selecting different sized stents 200 (i.e., stents that fully expand to different diameters). Table 1 below illustrates different exemplary porosities that the flow-diverting layer 202 can achieve by varying the size of the stent 200 (i.e., its fully expanded diameter) in a particular target vessel. It should be understood that modifying other aspects of the flow-diverting layer 202, such as the number of wires used, picks per inch (PPI), or wire size may also modify porosity. Preferably, the flow-diverting layer 202 has a porosity between about 45-70% when expanded.

Similar techniques are also possible with regard to the porosity of the stent 100. Preferably, the stent 100 has a porosity when expanded that is between about 75% and 95% and more preferably a range between about 80% and 88%. Put a different way, the stent 100 preferably has a metal surface area or percentage of metal between about 5% and 25% and more preferably between 12% and 20%.

TABLE 1

| No. of Wires | PPI | Fully Expanded Stent OD (mm) | Expansion Size in Target Vessel (mm) | Porosity of Flow-Diverting Layer 202 |
|---|---|---|---|---|
| 48 | 145 | 2.9 mm | Fully Expanded | 50% |
| 48 | 145 | 2.9 mm | 2.75 mm | 56% |
| 48 | 145 | 2.9 mm | 2.50 mm | 61% |
| 48 | 145 | 3.4 mm | Fully Expanded | 51% |
| 48 | 145 | 3.4 mm | 3.25 mm | 59% |
| 48 | 145 | 3.4 mm | 3.00 mm | 64% |
| 48 | 145 | 3.9 mm | Fully Expanded | 52% |
| 48 | 145 | 3.9 mm | 3.75 mm | 61% |
| 48 | 145 | 3.9 mm | 3.50 mm | 67% |

TABLE 1-continued

The stent 100 can be "oversized" or have a larger internal diameter relative to the outer diameter of the flow-diverting layer 202 when in a fully expanded position or a target vessel (having a target diameter). Preferably, the difference between the inner surface of the stent 100 and the outer surface of the flow-diverting layer 202 is between about 0.1 mm and about 0.6 mm (e.g., a gap between about 0.05 mm and about 0.3 mm between the two). Generally, the dual layer stent 200 can be slightly oversized for a patient's target vessel. In this respect, the outer stent 100 can slightly push into the tissue of the target vessel, allowing the "undersized" flow-diverting layer 202 to maintain a profile that is relatively close to or even touching the tissue of the vessel. This sizing can allow the stent 100 to better anchor within the vessel and closer contact between the flow-diverting layer 202 and vessel tissue. It should be further noted that this "oversizing" of the dual layer stent 200 can result in about a 10-15% increase in the porosity of the flow-diverting layer 202 relative to the fully expanded (and unobstructed) position of the flow-diverting layer 202, as seen in the exemplary data in Table 1.

The dual layer stent 200 can provide improved tracking and deployment performance, especially when compared to a stent of similar size and thickness to the flow-diverting layer 202. For example, tests have shown that a reduced amount of force is needed during deployment or retraction of the dual layer stent 200 from the delivery device in comparison to a stent similar to the flow-diverting layer alone. The inclusion of the outer stent 100 as part of the dual layer stent 200 reduces friction in the delivery system relative to the radial force and porosity of the stent 200.

Figure 19:
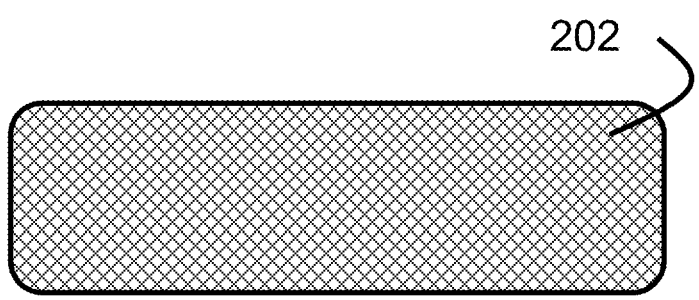
FIG. 19 illustrates a stent according to the present invention composed of a flow-diverting layer.

Preferably, the dual layer stent 200 can be deployed or retracted with between about 0.2 lbs and about 0.6 lbs of force. By including the stent 100 on the outside of the flow diverting layer 202, the deployment force can be reduced between about 10-50% as compared with the deploying/retracting the flow diverting layer 202 alone (i.e., a stand-alone layer 202 used by itself as seen in FIG. 19). Since less deployment force is required for the dual layer stent 200 as compared with a bare flow diverting layer 202, more desirable delivery characteristics can be achieved from a deployment device.

Figure 15:
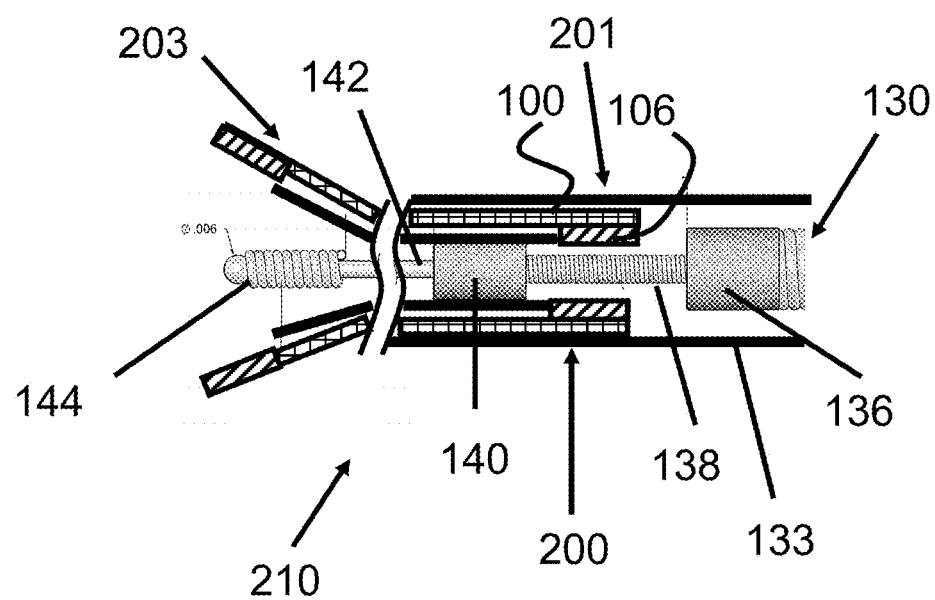
FIG. 15 illustrates a cross sectional view of a delivery system for the dual layer stent of FIGS. 12-14.

One exemplary deployment and retraction force test was performed on an exemplary dual layer stent 200 as seen in FIGS. 12-14 and a flow-diverting layer 202 alone, as shown in FIG. 19. The dual layer stent 200 required an average maximum deployment force of about 0.3 lbs and an average maximum retraction force of about 0.4 lbs. The stent of only a flow-diverting layer 202 had an average deployment force of about 0.7 lbs. Note that retraction of the flow-diverting layer 202 stent was not possible in the tests due to a lack of a locking or release mechanism (e.g., no coils 106 to contact marker band 140, as seen in FIG. 15). Preferably, the dual layer stent 200 includes differences in the diameter of the wire 102 of the outer stent 100, similar to those described for the embodiment of FIGS. 1-10. Specifically, the wire 102 making up the middle region of the stent 100 have a reduced diameter while the wire 102 at the ends (e.g., at loops 104) have a larger diameter than the middle region. For example, the middle region can be electropolished to reduce the diameter of wire 102 while the ends of the stent 100 can be protected from electropolishing, maintaining their original diameter. Put another way, the thickness of the stent 100 is thinner at a middle region. Note that this reduced thickness in the middle region is also applicable to embodiments of the outer stent that do not use wire (e.g., laser cut tube stent seen in FIG. 16). In test trials of an exemplary embodiment of the dual layer stent 200 with this diameter difference, relatively low deployment and retraction forces were demonstrated. These lower deployment and retraction forces can provide desirable tracking, deployment and retraction characteristics. Preferably, the wires 102 of the middle region are between about 0.0003 inch and about 0.001 inch smaller in diameter or thickness than the distal and/or proximal regions of the stent 100. Preferably, the wires 102 of the middle region are between about 10% to about 40% smaller in diameter or thickness than the distal and/or proximal regions of the stent 100 and most preferably about 25% smaller.

For example, one embodiment included ends composed of wire 102 having a diameter of about 0.0025 inch and a middle region composed of wire 102 having a diameter of about 0.0021 inch. This embodiment averaged a maximum average deployment force of about 0.3 lbs within a range of about 0.2-0.4 lbs and a maximum average retraction force of about 0.4 lbs within a range of about 0.3-0.4 lbs.

Another embodiment included ends composed of wire 102 having a diameter of about 0.0020 inch and a middle region composed of wire 102 having a diameter of about 0.0028 inch. This embodiment averaged a maximum average deployment force of about 0.2 lbs within a range of about 0.2-0.3 lbs and a maximum average retraction force of about 0.3 lbs in a range of about 0.3-0.4 lbs.

Another embodiment included ends composed of wire 102 having a diameter of about 0.0021 inch and a middle region composed of wire 102 having a diameter of about 0.0028 inch. This embodiment averaged a maximum average deployment force of about 0.4 lbs within a range of about 0.3-0.4 lbs and a maximum average retraction force of about 0.6 lbs in a range of about 0.5-0.6 inch.

Turning to FIG. 15, a delivery device 210 is shown according to the present invention for deploying the stent 200 within a patient. The delivery device 210 is generally similar to the previously described delivery device 135, including a sheath 133 disposed over a delivery pusher 130 to maintain the stent 200 in a compressed position over marker band 140.

As with the previous device, a proximal end 201 of the stent 200 is disposed over distal marker band 140 and proximal coil members 106 are positioned between marker bands 136 and 140. The stent 200 can be deployed by proximally retracting the sheath 201 relative to the pusher 130. The stent 200 can also be retracted (if it was not fully deployed/released) by retracting the pusher 130 in a proximal direction, thereby causing the marker band 140 to contact the proximal coil members 106, pulling the stent 200 back into the sheath 133.

As previously described, the proximal end 201 of the stent 200 includes attachment members 206 (not shown in FIG. 15) which connect the stent 100 with the flow-diverting layer 202. In this respect, as the sheath 133 is proximally retracted during deployment and a distal portion 203 of the dual layer stent 200 begins to radially expand, the stent 100 and the flow-diverting layer 202 can decrease in length at different rates.

A portion of the wire 105 can be woven along the length of the stent 100 in a distinctive pattern. This length can correspond to the length and position of the inner flow diverting layer 202, thereby indicating the length and position of the inner flow diverting layer 202 to the user during a procedure.

In another preferred embodiment according to the present invention, the flow-diverting layer 202 may be woven into the anchoring stent 100.

Figure 16:
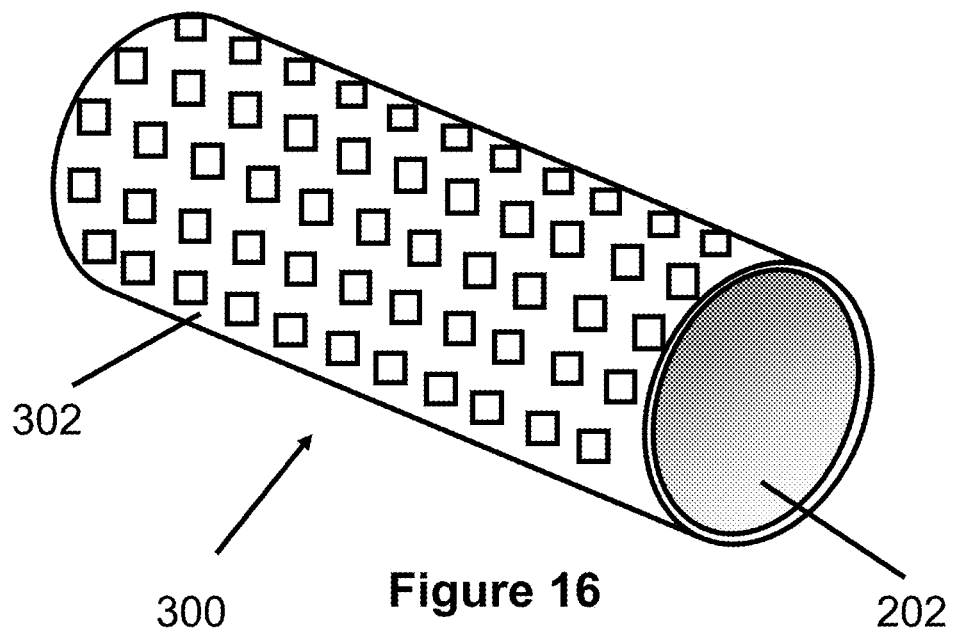
FIG. 16 illustrates a perspective view of dual layer stent having an outer stent layer formed from a tube or sheet of material.
Figure 17:
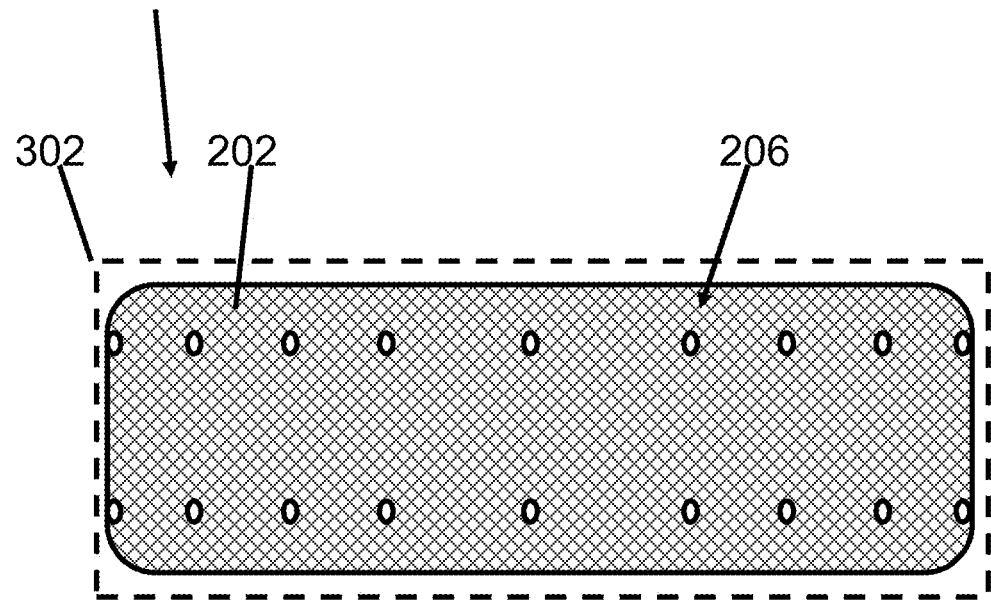
FIG. 17 illustrates a cross sectional view of the dual layer stent of FIG. 15 showing various optional attachment points of both layers of the dual layer stent.

FIG. 16 illustrates another embodiment according to the present invention of a dual layer stent 300 comprising an inner flow-diverting layer 202 and an outer stent 302. Preferably, the outer stent 302 is formed by cutting a pattern (e.g., laser cutting or etching) in a sheet or tube composed of a shape memory material (e.g. Nitinol). FIG. 16 illustrates a pattern of a plurality of diamonds along the length of the outer stent 302. However, it should be understood that any cut pattern is possible, such as a plurality of connected bands, zig-zag patterns, or wave patterns.

The cross sectional view of the dual layer stent 300 illustrates a plurality of exemplary positions for attachment member 206 to connect the outer stent 302 and inner flow-diverting layer 202. As with any of the previously described embodiments, the attachment members 206 (or other methods of attachment such as welding or adhesive) can be located at one or more of the exemplary locations shown. For example, attachment members 206 may be located at the proximal end, distal end, or the middle. In another example, attachment members 206 can be located at both the proximal and distal ends. Alternately, no attachment members 206 or attachment mechanism are used to attach the inner flow-diverting layer 202 with the outer stent 302.

Figure 18:
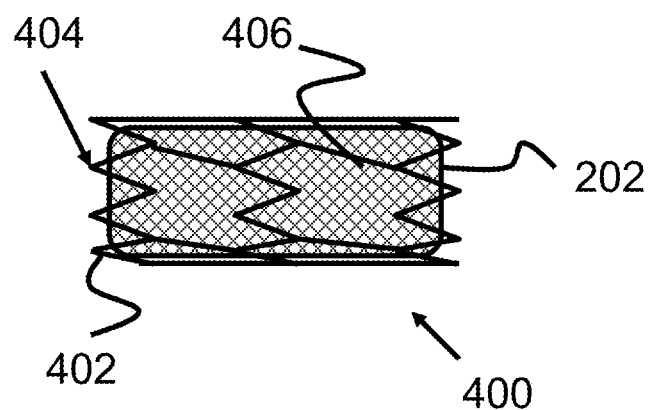
FIG. 18 illustrates another preferred embodiment of a dual layer stent according to the present invention.

FIG. 18 illustrates another embodiment of a dual layer stent 400 according to the present invention. The stent 400 comprises an inner flow-diverting layer 202 attached to an outer stent 402. The outer stent 402 comprises a plurality of radial, zigzag bands 404 that are bridged or connected via longitudinal members 406. Preferably, the stent 402 can be created by welding a plurality of members together, laser cutting or etching this pattern into a sheet or tube, or using vapor deposition techniques. As with previous embodiments, the flow-diverting layer 202 can be attached to the outer stent 402 near the distal end, proximal end, middle region, or any combination of these locations.

As best seen in FIGS. 12 and 13, the flow-diverting layer 202 preferably has a length that extends near the ends of the main body portion of stent 100 and stops near the formation of the loops 104. However, the flow-diverting layer 202 can alternately include any range of lengths and positions relative to the stent 100. For example, FIG. 20 illustrates a dual layer stent 200A in which the flow-diverting layer 202 is shorter in length than the stent 100 and longitudinally centered or symmetrically positioned.

In another example, FIG. 21 illustrates a dual layer stent 200B in which the flow-diverting layer 202 is longer in length than the stent 100. While the flow-diverting layer 202 is shown as being longitudinally centered within the stent 100, asymmetrical positioning of the flow-diverting layer 202 is also contemplated.

In yet another example, FIG. 22 illustrates a dual layer stent 200C in which a flow-diverting layer 202 is shorter in length than the stent 100 and asymmetrically positioned within the stent 100. In this example, the flow-diverting layer 202 is positioned along the proximal half of the stent 100, however, the flow-diverting layer 202 may also be positioned along the distal half of the stent 100. While the flow-diverting layer 202 is shown extending about one half of the length of the stent 100, the flow-diverting layer 202 may also span one third, one quarter or any fractional portion of the stent 100.

Figure 23:
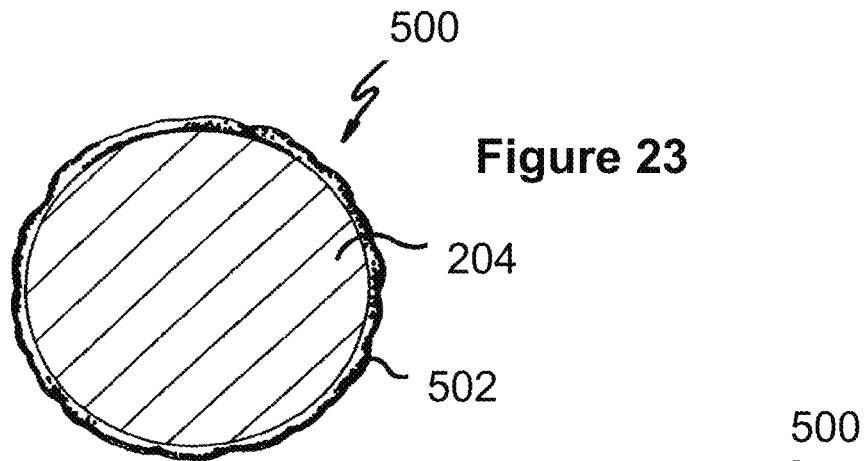
FIGS. 23 and 24 illustrate an expansile wire for use with a flow-diverting layer according to the present invention.
Figure 24:
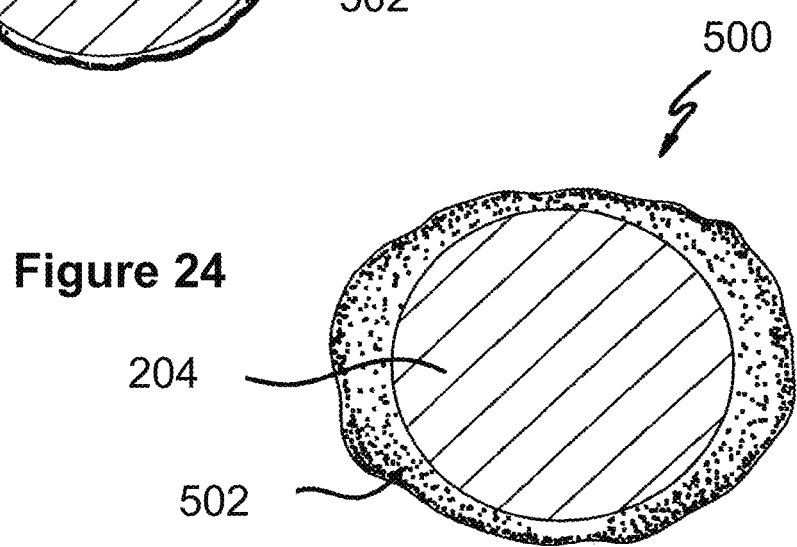
Figure 25:
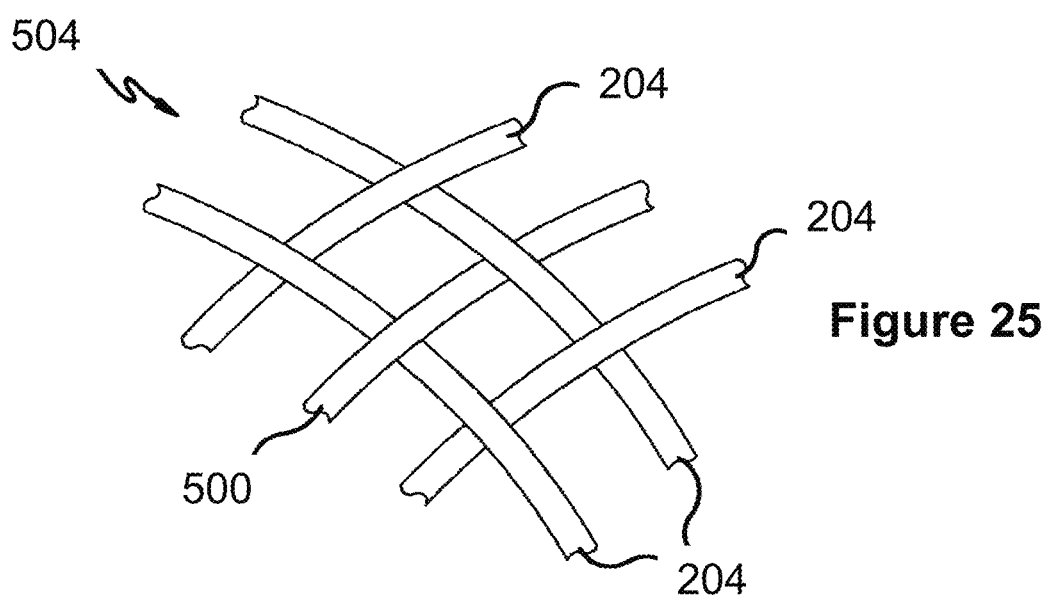
FIG. 25 illustrates a portion of a flow-diverting layer having an expansile wire incorporated into its structure.
Figure 26:
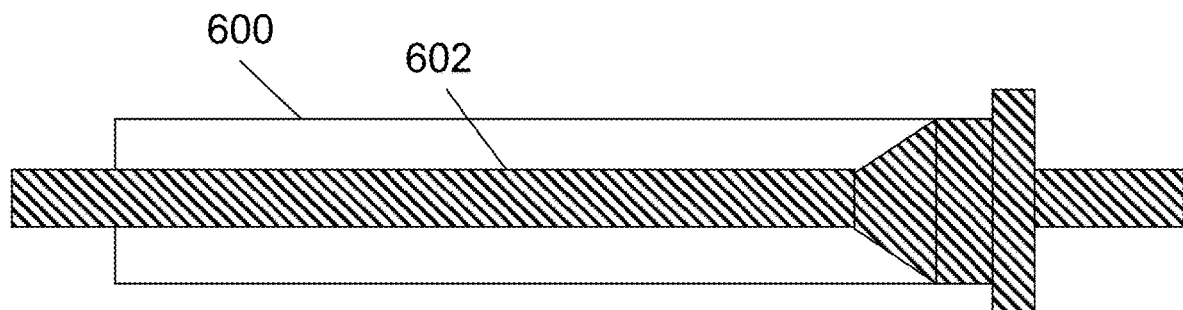
FIG. 26-29 illustrate a process according to the present invention for creating a polymer stent or stent layer.

Turning to FIGS. 23-25, the flow-diverting layer 202 can be composed of one or more expansile wires 500 or filaments. Preferably, the expansile wires 500 are composed of the previously described wires 204 that are coated with a hydrogel coating 502 that expands in a patient's vessel. The wires 204 may be composed of a shape memory metal (e.g., nitinol), a shape memory polymer, nylon, PET or even entirely of hydrogel. As seen in FIG. 25, the hydrogel wires 500 can be woven amongst wires 204 which are not coated with hydrogel. Alternately, partial lengths of the wires can be coated with hydrogel so as to coat only a specific region of the flow-diverting layer 202 (e.g., the center region).

In any of the previous embodiments, one or more of the stent layers (e.g., stent 100 or flow diverting layer 202) can be mostly composed of a polymer (e.g., a hydrogel, PET (Dacron), nylon, polyurethane, Teflon, and PGA/PGLA). Generally, a polymer stent can be manufactured by the free radical polymerization of a liquid prepolymer solution within a container of a desired shape.

One exemplary polymer stent manufacturing technique can be seen in FIGS. 26-29. Starting with FIG. 26, a generally cylindrical mandrel 602 is placed within a tube 600. Preferably, the mandrel 602 can create a fluid-tight seal on at least one end of the tube 600 and preferably the opposing end of the tube 600 is also closed.

Figure 27:
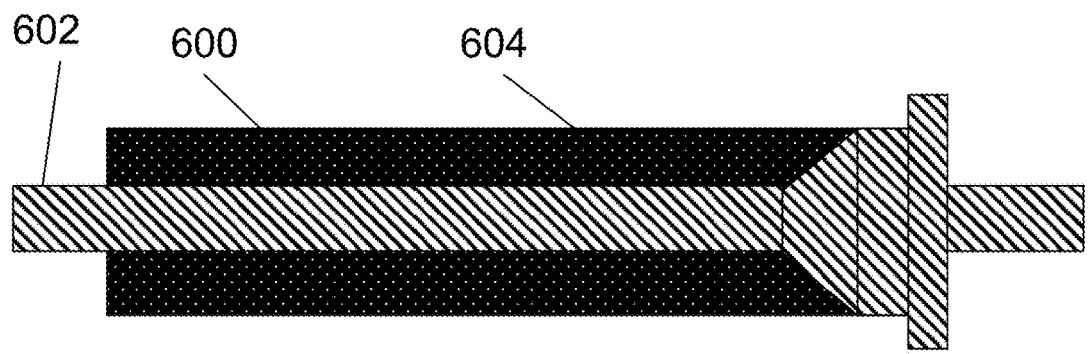
Figure 28:

In FIG. 27, a liquid prepolymer is injected into the space between the mandrel 602 and the tube 600. Polymerization is induced in the prepolymer solution (e.g., heating at 40-80° C. for 12 hours). Once polymerized, the tube 600 and mandrel 602 are removed from the solid polymer tube 606, shown in FIG. 28. This tube 606 can be washed to eliminate residual monomers and dried over a mandrel to maintain shape.

Figure 29:
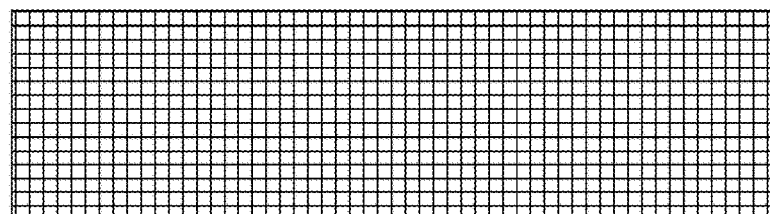

Finally, the polymer tube 606 can be laser cut, CNC machined, etched or otherwise shaped into a desired pattern, as seen in FIG. 29. The length and thickness of the final stent can also be modified during the manufacturing process by changing the diameter or length of the tube 606 or the mandrel 602.

Figure 30:
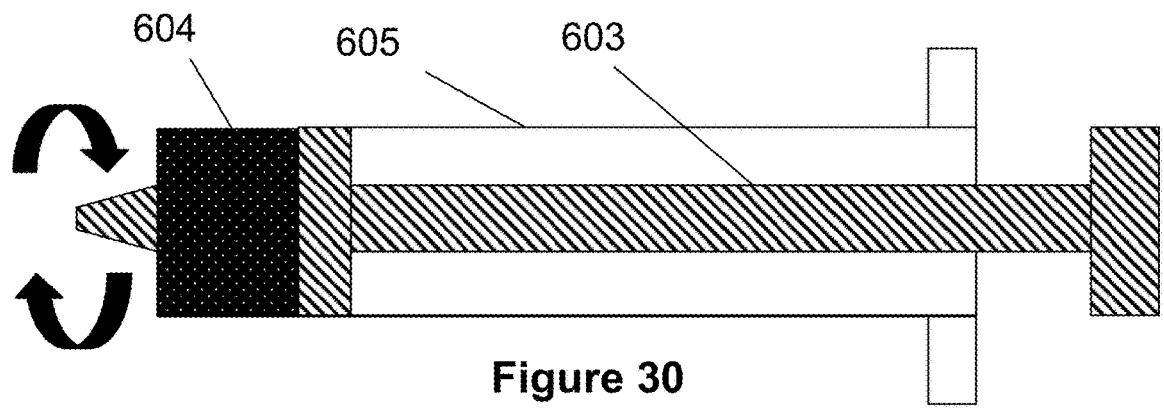
FIG. 30 illustrates another process according to the present invention for creating a polymer stent or stent layer; and, FIGS. 31-36 illustrate another process according to the present invention for creating a polymer stent or stent layer.

In another exemplary stent manufacturing process seen in FIG. 30, centrifugal force is used to disperse the prepolymer solution along the inside of a syringe tube 605. Specifically, a plunger 603 is positioned in the tube 605 and a predetermined amount of prepolymer solution 604 is taken into the syringe tube 605. The syringe tube 605 is connected to a mechanism that causes the tube 605 to spin in a horizontal orientation along a longitudinal axis of the tube 605 (e.g., an overhead stirrer positioned horizontally with its rotating member connected to the tube 605).

Once the tube 605 achieves a sufficient rotational speed (e.g., about 1500 rpm), the syringe plunger 603 is pulled toward the end of the tube 605, taking in a gas such as air. Since the prepolymer solution now has more space to spread out, the centrifugal force causes an even coating to form on the wall of the tube 605. Polymerization can be initialed using a heat source (e.g., a heat gun) and then heated (e.g., 40-80° C. for 12 hours). The solid polymer tube can then be removed from the tube 605, washed to eliminate residual monomers, dried on a mandrel, and then laser cut, CNC machined, etched or otherwise shaped into a desired pattern.

Figure 31:
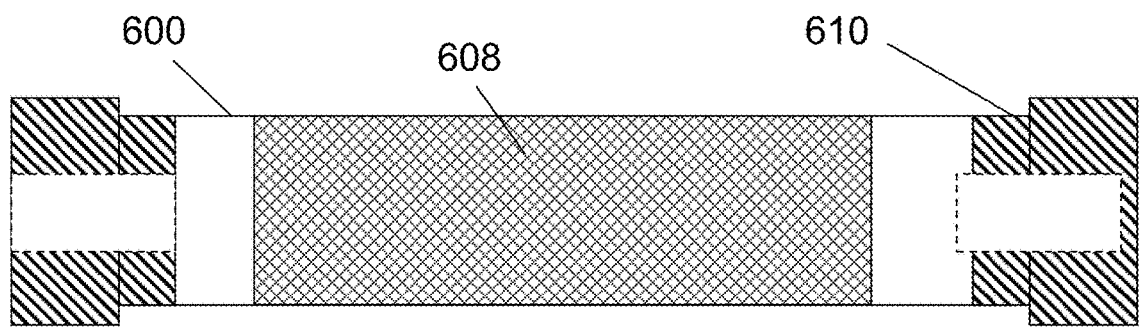

FIGS. 31-36 illustrate yet another exemplary process for creating a polymer stent according to the present invention. Turning first to FIG. 31, a plastic or degradable rod 608 is placed in tube 600 and luer adapters 610 are connected to each opening of the tube 600. The rod 608 has an engraved or depressed pattern (e.g., created by laser machining, CNC machining or other suitable method) on its outer surface in the patter desired for the final stent. When the rod 608 is placed in the tube 600, these patterns form channels that are later filled by the prepolymer 604. In other words, the outer diameter of the rod 608 and the inner diameter of the tube 600 are such that the prepolymer 604 is prevented from moving outside the channels or patterned area.

Figure 32:
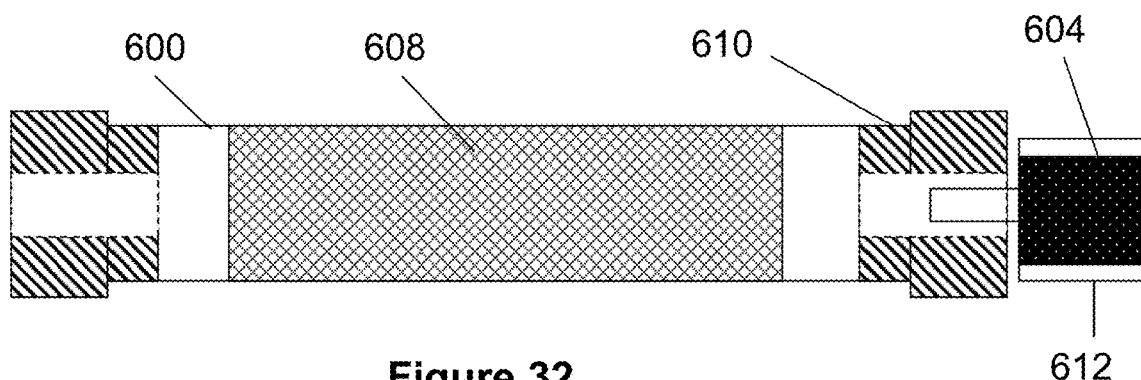
Figure 33:
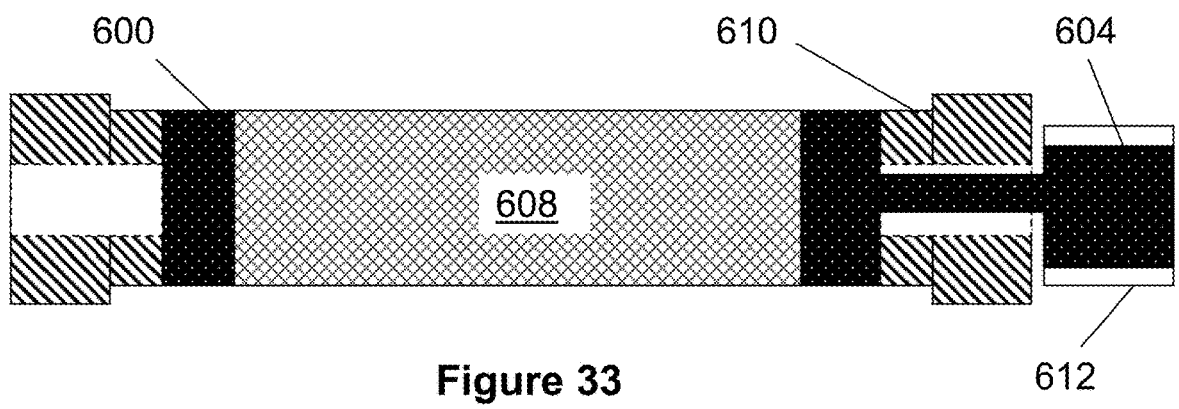

As seen FIG. 32, a syringe 612 is inserted into a luer adapter 610 and prepolymer solution 604 is injected into the tube 600 as seen in FIG. 33. The prepolymer solution 604 fills into the pattern on the surface of the rod 608. The syringe 612 is removed from the luer adapter 610 and polymerization is completed by heating the prepolymer solution 604 (e.g., 40-80° C. for about 12 hours).

Figure 34:
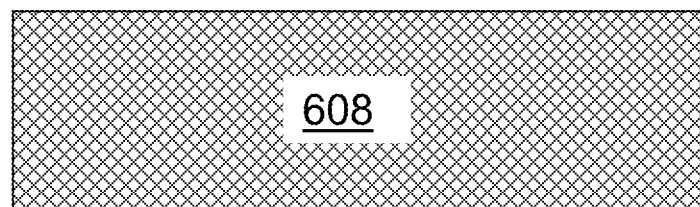
Figure 35:
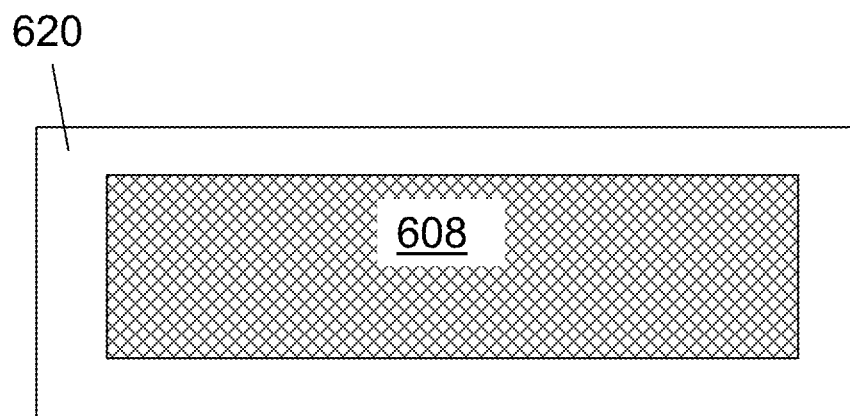
Figure 36:
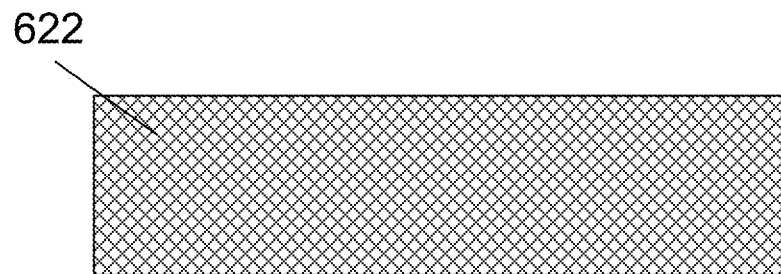

The rod 608 is removed from the tube 600 as seen in FIG. 34 and placed in an organic solvent bath 622 as seen in FIG. 35. The organic solvent bath 622 dissolves the rod 608, leaving only the polymer stent 622 (FIG. 36) having the same pattern as the surface of the rod 608.

It should be noted that different aspects of the stent 622 can be controlled by changing the pattern on the surface of the rod 608, the diameter of the rod 608 and the tube 600, the length of the rod 608 and tube 600 and similar dimensions. Additional modification is also possible by laser cutting, CNC machining, etching, or similar processes.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A stent comprising:
   one or more wires woven into a tubular configuration;
   a plurality of first regions of the one or more wires having a first thickness; and,
   a plurality of second regions of the one or more wires having a second thickness that is reduced relative to the first thickness;
   wherein a profile layer thickness of the stent decreases when in a compressed configuration due to the plurality of second regions being located at overlapping wire locations when in the compressed configuration, wherein the profile layer thickness of the stent in the compressed configuration is decreased compared to the profile layer thickness of the stent in an expanded configuration.

2. The stent of claim 1, wherein one or more of the plurality of first regions are located at one or more terminal ends of the stent.

3. The stent of claim 1, wherein the stent utilizes an inner layer and an outer layer.

4. The stent of claim 1, wherein the stent utilizes a single layer.

5. The stent of claim 4, wherein the one or more wires consist of one wire.

6. The stent of claim 1, further comprising looped ends.

7. The stent of claim 6, wherein the first region also includes the looped ends.

8. A stent comprising:
one or more wires forming a tubular braid;
a plurality of first regions of the one or more wires having a first thickness; and,
a plurality of second regions of the one or more wires having a second thickness that is reduced relative to the first thickness;
wherein a profile layer thickness of the stent decreases when in an expanded configuration due to the plurality of second regions being located at overlapping wire locations when in the expanded configuration, wherein the profile layer thickness of the stent in the expanded configuration is decreased compared to the profile layer thickness of the stent in a compressed configuration.

9. The stent of claim 8, wherein the first region further comprises one or more terminal ends of the stent.

10. The stent of claim 8, wherein the stent utilizes an inner layer and an outer layer.

11. The stent of claim 8, wherein the stent utilizes a single layer.

12. The stent of claim 11, wherein the one or more wires consist of one wire.

13. The stent of claim 8, further comprising looped ends.

14. The stent of claim 13, wherein the first region comprises the looped ends.

15. A stent comprising:
one or more wires, including a multi-thickness wire, woven into a tubular configuration,
wherein the multi-thickness wire comprises:
one or more first regions having a circular cross section with a first diameter; and
one or more second regions connected to the first region and having a circular cross section with a second diameter that is less than the first diameter;
wherein a profile layer thickness of the stent decreases only when in a compressed configuration and in an expanded configuration due to one or more of the second regions being located at overlapping wire locations only when the stent is in the compressed configuration or in the expanded configuration.

16. The stent of claim 15, wherein one or more of the one or more first regions are located at one or more terminal ends of the stent.

17. The stent of claim 15, wherein the stent utilizes an inner layer and an outer layer.

18. A stent comprising:
one or more wires woven into a tubular configuration;
a plurality of first regions of the one or more wires having a first thickness; and,
a plurality of second regions of the one or more wires having a second thickness that is reduced relative to the first thickness in at least one direction;
wherein the plurality of first regions and the plurality of second regions are interwoven along a substantial length of the stent in an axial direction; and
wherein a profile layer thickness of the stent decreases only when in a compressed configuration and in an expanded configuration due to the plurality of second regions being located at overlapping wire locations only when the stent is in the compressed configuration or in the expanded configuration.

19. The stent of claim 18, wherein the stent has a substantially uniform porosity along the substantial length in an axial direction.

20. The stent of claim 18, wherein the stent has a substantially uniform radial force along the substantial length in an axial direction.

* * * * *